United States Patent
Alt et al.

(10) Patent No.: US 10,328,056 B2
(45) Date of Patent: Jun. 25, 2019

(54) PRIMING OF PANCREATIC TUMOR CELLS AND CANCER STEM CELLS TO TRAIL-INDUCED APOPTOSIS

(71) Applicant: Alliance of Cardiovascular Researchers, New Orleans, LA (US)

(72) Inventors: Eckhard U Alt, Houston, TX (US); Alejandro Recio Boiles, Bronx, NY (US); Matthias Ilmer, Munich (DE)

(73) Assignee: Alliance of Cardiovascular Researches, New Orleans, LA (US)

( * ) Notice: Subject to any disclaimer, the term of this patent is extended or adjusted under 35 U.S.C. 154(b) by 0 days.

(21) Appl. No.: 15/329,970

(22) PCT Filed: Jul. 29, 2015

(86) PCT No.: PCT/US2015/042739
§ 371 (c)(1),
(2) Date: Jan. 27, 2017

(87) PCT Pub. No.: WO2016/019062
PCT Pub. Date: Feb. 4, 2016

(65) Prior Publication Data
US 2017/0258765 A1      Sep. 14, 2017

Related U.S. Application Data

(60) Provisional application No. 62/030,547, filed on Jul. 29, 2014.

(51) Int. Cl.

| | |
|---|---|
| A61K 9/00 | (2006.01) |
| A61K 38/17 | (2006.01) |
| A61K 38/19 | (2006.01) |
| C07K 16/24 | (2006.01) |
| C07K 16/28 | (2006.01) |
| A61K 39/395 | (2006.01) |
| A61K 31/416 | (2006.01) |
| A61K 45/06 | (2006.01) |
| A61K 35/35 | (2015.01) |
| A61K 35/76 | (2015.01) |
| C12N 7/00 | (2006.01) |

(52) U.S. Cl.
CPC .......... *A61K 31/416* (2013.01); *A61K 9/0019* (2013.01); *A61K 9/0053* (2013.01); *A61K 35/35* (2013.01); *A61K 35/76* (2013.01); *A61K 38/1761* (2013.01); *A61K 38/1793* (2013.01); *A61K 38/191* (2013.01); *A61K 39/3955* (2013.01); *A61K 39/39541* (2013.01); *A61K 45/06* (2013.01); *C07K 16/244* (2013.01); *C07K 16/2866* (2013.01); *C12N 7/00* (2013.01); *C07K 2317/76* (2013.01)

(58) Field of Classification Search
None
See application file for complete search history.

(56) References Cited

U.S. PATENT DOCUMENTS

| 8,163,709 B2* | 4/2012 | Kodym | A61K 31/7105 |
| | | | 514/44 A |
| 2005/0153337 A1* | 7/2005 | Manoharan | C12N 15/111 |
| | | | 435/6.14 |
| 2007/0003531 A1* | 1/2007 | Mukherji | C07K 14/4747 |
| | | | 424/93.21 |
| 2009/0131317 A1* | 5/2009 | Angell | C07K 14/70575 |
| | | | 514/1.1 |
| 2010/0179141 A1* | 7/2010 | Belanger | C07D 213/81 |
| | | | 514/233.8 |

FOREIGN PATENT DOCUMENTS

WO    WO2009140469    * 11/2009    ........... A61K 39/395

OTHER PUBLICATIONS

Chakravarthy et al. Role of the eIF4E binding protein 4E-BP1 in regulation of the sensitivity of human pancreatic cancer cells to TRAIL and celastrol-induced apoptosis. 105, 414-429, 2013. (Year: 2013).*

Bai, X, et al "Both cultured and freshly isolated adipose tissue-derived stem cells enhace cardiac function after acute myocardial infarction" Eur Heart J. 31 (2010) 489-501.

Bai X, Alt E, "Myocardial regeneration potential of adipose tissue-derived stem cells" Biochemical and Biophysical Research Communications 401 (2010) 321-326.

Bennett BL, et al "SP600125, an anthrapyrazolene inhibitor of Jun N-terminal kinase" Proc Natl Acad Sci USA, 98 (24) (2001) 13681-13686.

Chakravarthy et al "Role of eIF4E binding protein 4E-BP1 in regulation of the sensitivity of human pancreatic cancer cells to TRAIL and celastrol-included apoptosis" Biol. Cell 105 (2013) 414-429.

Davis CC, et al "Impaired JNK Signaling Cooperates with KrasG12D Expression to Accelerate Pancreatic Ductal Adenocarcinoma" Cancer Res. 74 (12) (2014) 3344-3356.

Hartwig W, et al "Improvement of surgical results for pancreatic cancer" Lancelot Oncol. 14 (2013) e476-85.

Jones S, et al "Core Signaling Pathways in Human Pancreatic Cancers Revealed by Global Genomic Analyses" Science 321 (5897) (2008) 1801-1806.

Lemke J, et al "TRAIL signaling is mediated by DR4 in pancreatic tumor cells despite the expression of functional DR5" J Mol Med. 88 (2010) 729-40.

Lonardo E, et al "Nodal/Activin Signaling Drives Self-Renewal and Tumorigenicity of Pancreatic Cancer Stem Cells and Provides a Target for Combined Drug Therapy" Cell Stem Cell 9 (2011) 433-446.

(Continued)

*Primary Examiner* — Elly-Gerald Stoica
(74) *Attorney, Agent, or Firm* — Blank Rome LLP

(57) ABSTRACT

This invention relates generally to compositions and methods for treatment of pancreatic cancer. The present invention relates more particularly to use of JNK inhibition together with administration of TRAIL to selectively suppress cancer stem cells.

9 Claims, 22 Drawing Sheets

(56) References Cited

OTHER PUBLICATIONS

Morris JP, et al "KRAS, Hedgehog, Wnt and the twisted developmental biology of pancreatic ductal adenocarcianoma" Nat Rev Cancer 10 (10) (2010) 683-695.
Okada M, et al "Targeting the K-Ras—JNK axis eliminates cancer stem-like cells and prevents pancreatic tumor formation" Oncotarget 5 (13) (2014) 5100-5112.
Olson P, Hanahan D. "Breaching the Cancer Fortress" Science 324 (2009) 1400-1401.
Recio-Boiles, A, et al. "JNK pathway inhibition selectively primes pancreatic cancer stem cells to TRAIL-induced apoptosis without affecting the physiology of normal tissue resident stem cells" Oncotarget 7 (9) (2016) 9890-9906.
Takahashi R, et al "Therapeutic effect of c-Jun N-terminal kinase inhibition on pancreatic cancer" Cancer Science 104 (2013) 337-44.
Todaro M, et al "Colon Cancer Stem Cells Dictate Tumor Growth and Resist Cell Death by Production of Interleukin-4" Cell Stem Cell. (2007) 389-402.
Wilson C, et al "Interleukin-8 signaling attenuates TRAIL-and chemotherapy-induced apoptosis through transcriptional regulation of c-FLIP in prostate cancer cells" Mol Cancer Ther. 7 (9) (2008) 2649-61.
Yoon C-H, et al "c-Jun N-terminal kinase has a pivotal role in the maintenance of self-renewal and tumorigenicity in glioma stem-like cells" Oncogene 31 (2012) 4655-66.

* cited by examiner

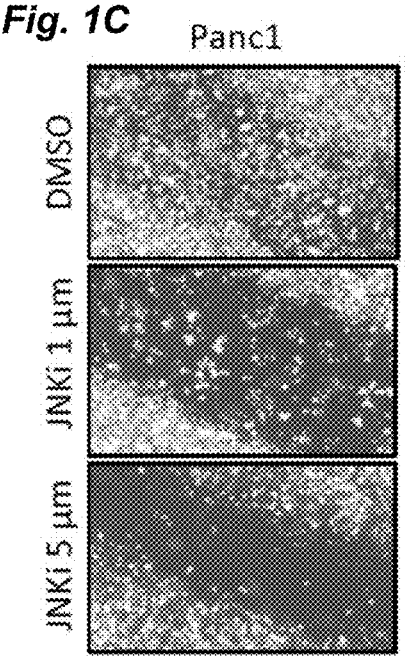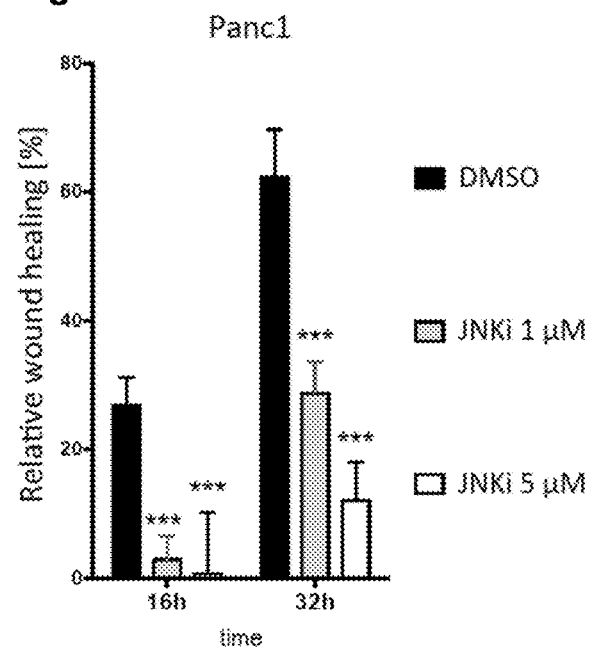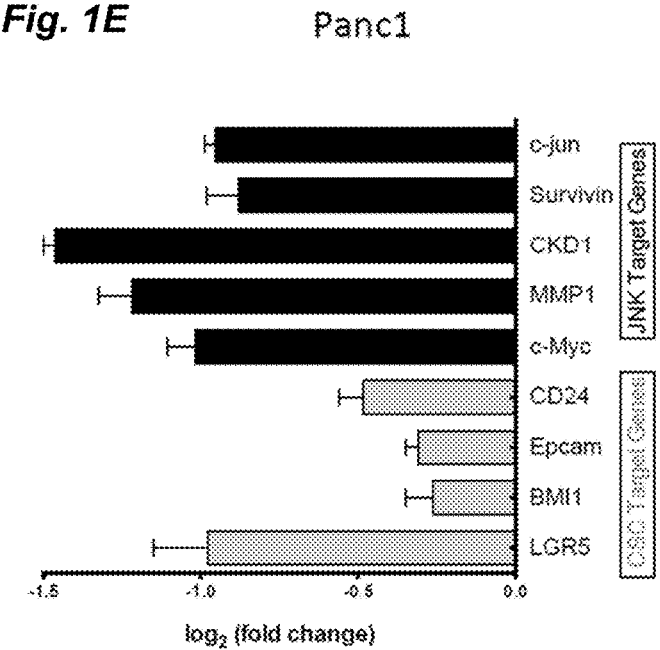

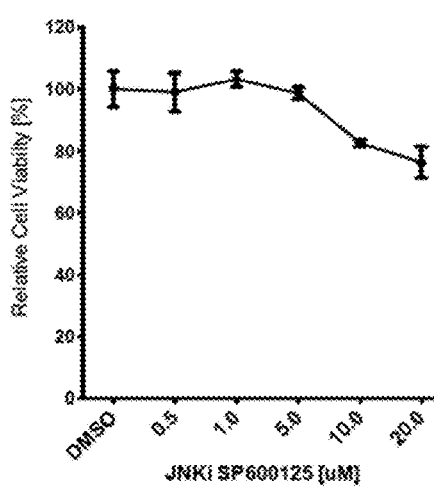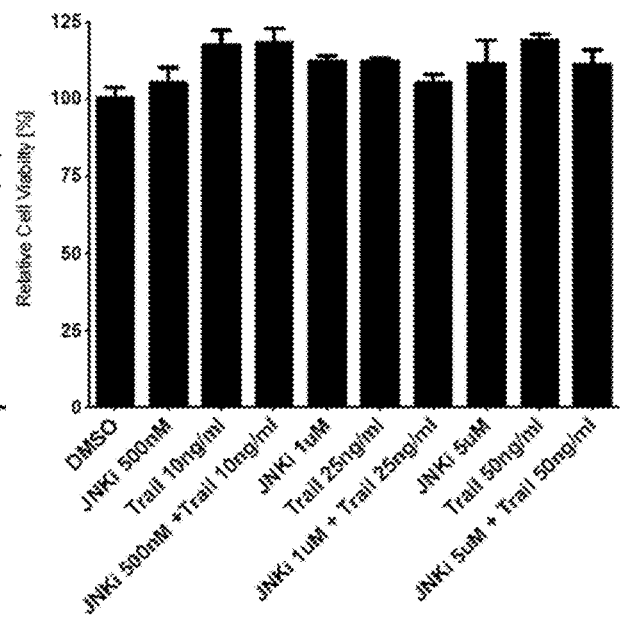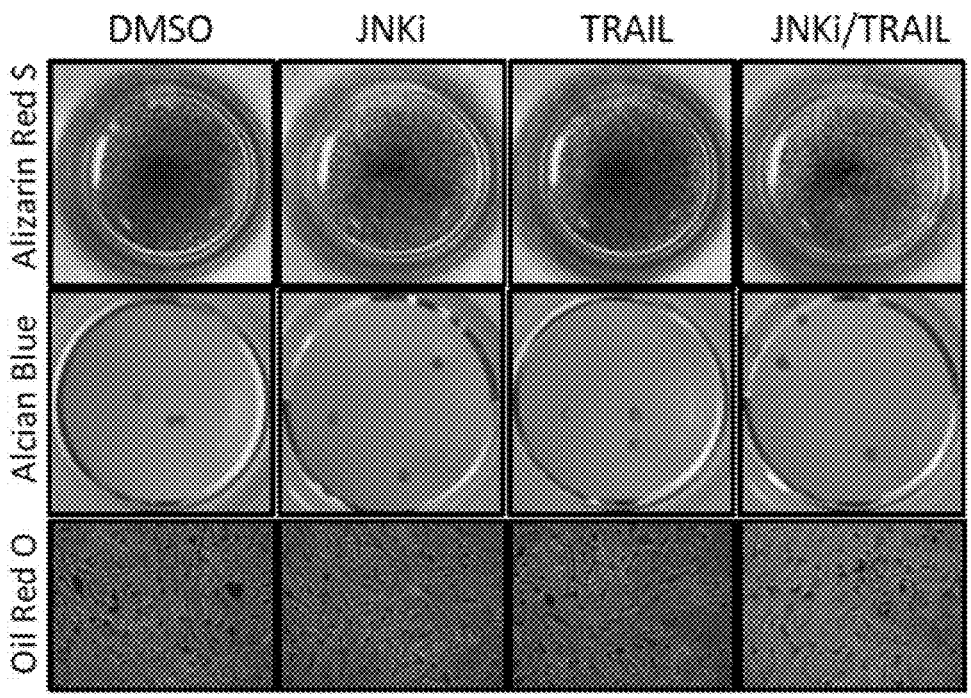

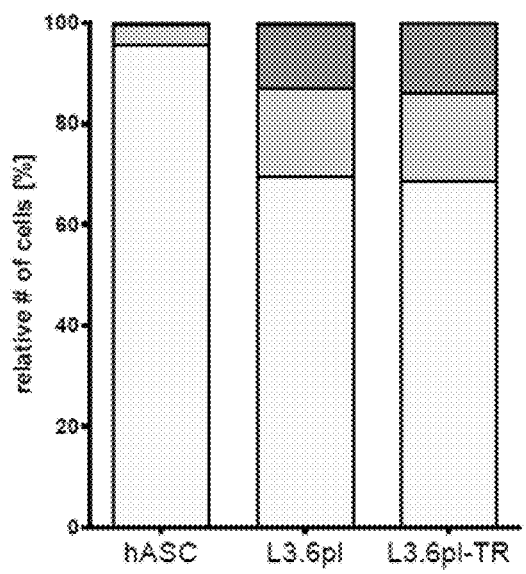
FIG. 8D DMSO
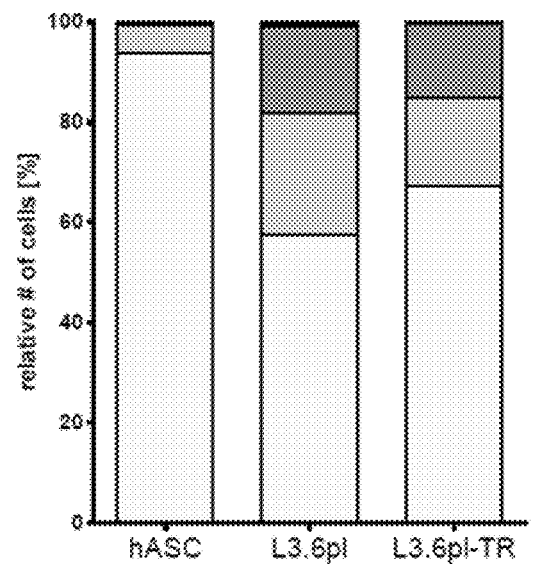
FIG. 8E JNKi
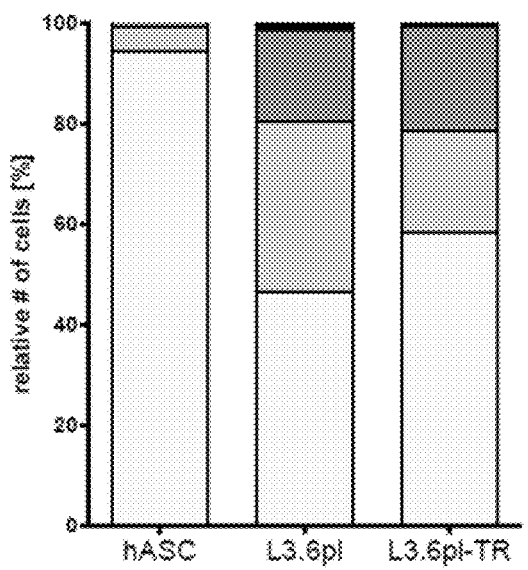
FIG. 8F TRAIL
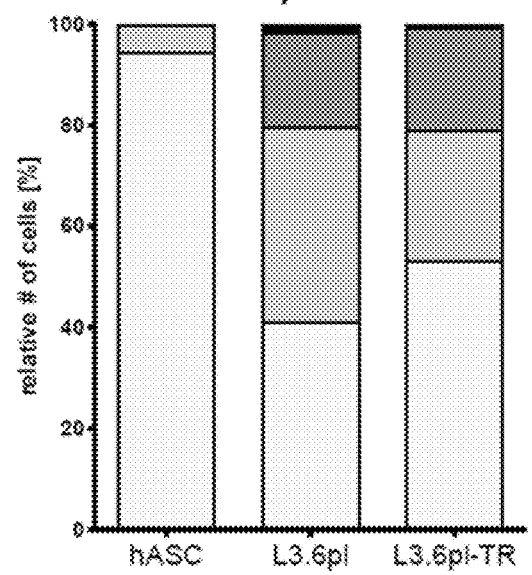
FIG. 8G JNKi/TRAIL

PRIMING OF PANCREATIC TUMOR CELLS AND CANCER STEM CELLS TO TRAIL-INDUCED APOPTOSIS

CROSS REFERENCE TO RELATED APPLICATIONS

This application claims priority based on PCT/US2015/042739, filed Jul. 29, 2015, which in turn claims priority based on U.S. Provisional Application Ser. No. 62/030,547 filed Jul. 29, 2014, which are incorporated herein by reference.

FIELD OF THE INVENTION

This invention relates generally to compositions and methods for treatment of pancreatic cancer. The present invention relates more particularly to use of JNK inhibition together with administration of TRAIL to suppress cancer stem cells.

BACKGROUND OF THE INVENTION

Without limiting the scope of the invention, its background is described in connection with existing treatments for pancreatic ductal adenocarcinoma (PDAC). PDAC is typically associated with drug resistance, metastasis, and dismal clinical outcomes. To date, surgery is the only treatment that offers patients with PDAC a chance for cure. See Hartwig W, et al. "Improvement of surgical results for pancreatic cancer" *Lancet Oncol.* 14 (2013) e476-85. Early detection of this stroma-rich, desmoplastic neoplasm is challenging because of long symptom-free intervals. See Olson P, Hanahan D. "Breaching the Cancer Fortress" *Science.* 324 (2009) 1400-1. Although extensive efforts have been made to advance the molecular and clinical understanding of PDAC, drug-based treatment regimens have been unsatisfactory so far, and 5-year survival has improved only slightly over the past decades.

PDAC is associated with several well-described mutations in a subset of genes including those that encode KRAS, SMAD4, and p53. See Morris J P, et al. "KRAS, Hedgehog, Wnt and the twisted developmental biology of pancreatic ductal adenocarcinoma" *Nat Rev Cancer* 10 (2010) 683-95. PDAC also exhibits additional mutations that affect various pathways. See Jones S, et al. "Core Signaling Pathways in Human Pancreatic Cancers Revealed by Global Genomic Analyses" *Science* 321 (2008) 1801-6. Spontaneous genetic alterations make a successful treatment relatively difficult since they provide pancreatic tumors escape routes from therapy.

From the foregoing it is apparent the there is a need in the art for improved therapeutic regimens that are effectively directed to reducing the metastatic potential of cancer stem cells without adversely affecting normal stem cells.

SUMMARY

The present inventors undertook to identify selective molecular pathways that would be highly effective in inhibiting cancer growth, specifically that of cancer stem cells. Disclosed herein is the identification of a treatment regime that relies on downregulation of the decoy TRAIL receptors 1 and 2 (DcR1/2) without affecting the physiology of normal tissue-resident stem cells even under hypoxic conditions that resemble the desmoplastic environment of PDACs.

In one embodiment provided herein a method of treating pancreatic cancer in a patient is provided that includes administration of a low-dose of a c-Jun N-terminal kinase (JNK) inhibitor in combination with a low-dose of a TNF-related apoptosis-inducing ligand ("TRAIL"). In certain embodiments the low-dose of the JNK inhibitor is a dose that corresponds to an in vitro dose that will reduce cell viability in a pancreatic cell line by 20% or less. The relevant dose of the JNK inhibitor will depend on the pharmacologic properties of the specific inhibitor and such dose may be obtained empirically and may differ with different chemical moieties and physiological half-lives. In certain specifically exemplified embodiments, the low-dose of TRAIL is a dose that corresponds to a dose of 1 mg/kg or less.

In certain embodiments the JNK inhibitor is administered orally and the TRAIL is administered by intraperitoneal injection. In other embodiments, relatively high local concentrations of TRAIL are provided without systemic toxicity by isolating a stem cell population from the patient and transforming the stem cell population with a genetic construct that induces increased TRAIL production by stem cell, thereby obtaining a genetically engineered stem cell population that overproduces TRAIL. The genetically engineered stem cell population that overproduces TRAIL is introduced into the cancer patient whereby increased levels of TRAIL are produced in a local environment where cancer cells are located in the patient. The stem cell population may be a population of adipose derived stem cells isolated from the patient.

In other embodiments a method of treating pancreatic cancer is provided including systemic administration of a low-dose of a c-Jun N-terminal kinase (JNK) inhibitor in combination with localized administration of a TNF-related apoptosis-inducing ligand ("TRAIL") in an organ or region of the patient where a tumor is present. The localized administration is obtained in some embodiments by introducing a recombinant TRAIL into a vessel or duct in direct fluid communication with the organ or region of the patient where the tumor is present. In other embodiments, the localized administration of TRAIL is obtained by injecting a virus encoding and expressing a recombinant TRAIL into the organ or region in the patient where the tumor is present.

The low-dose of the JNK inhibitor and the low-dose of TRAIL are doses that do not significantly impact a rate of growth of the cancer if administered individually but rather act synergistically as discovered by the present inventors. In particular the present inventors discovered a particular sensitivity of cancer stem cells to this combination. This finding and its consequent application is particularly important because cancer stem cells are resistant to chemotherapy in part on the basis of cellular pumps that are able to reduce intracellular concentrations of toxic agents. Accordingly and specifically, in one embodiment of the invention, JNK inhibition by administration of INK inhibitors is combined with administration or induction of TRAIL as a novel and selective therapeutic approach for controlling pancreatic cancer stem cells with minimal effect on normal stem cells.

In certain embodiments the effects of the combination of low doses of INK and TRAIL inhibitors are combined with an antagonist to IL-8 and/or its receptor CXCR1.

BRIEF DESCRIPTION OF THE DRAWINGS

For a more complete understanding of the present invention, including features and advantages, reference is now made to the detailed description of the invention along with the accompanying figures:

FIGS. 1A-1G demonstrate the results of experiments showing that PDAC cells depend on JNK signaling for growth and survival.

FIGS. 8A-8G demonstrate the results of experiments showing that JNKi does not affect the physiology and function of normal tissue-resident stem cells (ASC). FIG. 8A: MTT proliferation assay of adipose tissue-derived stem cells (ASCs) with increasing doses of JNKi. Experiment was performed in triplicate. FIG. 8B: Relative cell survival of ASCs after exposure to JNKi and/or TRAIL with doses up to five times those used in pancreatic cancer treatment. Experiment was performed in triplicate. FIG. 8C: Differentiation assays of ASCs into adipocytes, chondrocytes or osteoblasts. Confirmation of terminal differentiation was carried out by standard staining procedures (Alizarin Red, Alcian Blue, and Oil Red O). FIG. 8D-8G: hASC, L3.6pl or L3.6pl-TR were cultured under hypoxic conditions (95% $N_2$ and 5% $CO_2$ mixture) with DMSO, JNKi, TRAIL or JNKi/TRAIL for 48 h. Cell death (necrosis, black) and apoptosis (early, light grey; late, dark grey) were evaluated by Annexin V-FITC/PI-staining.

DETAILED DESCRIPTION OF THE INVENTION

Figure 1A:
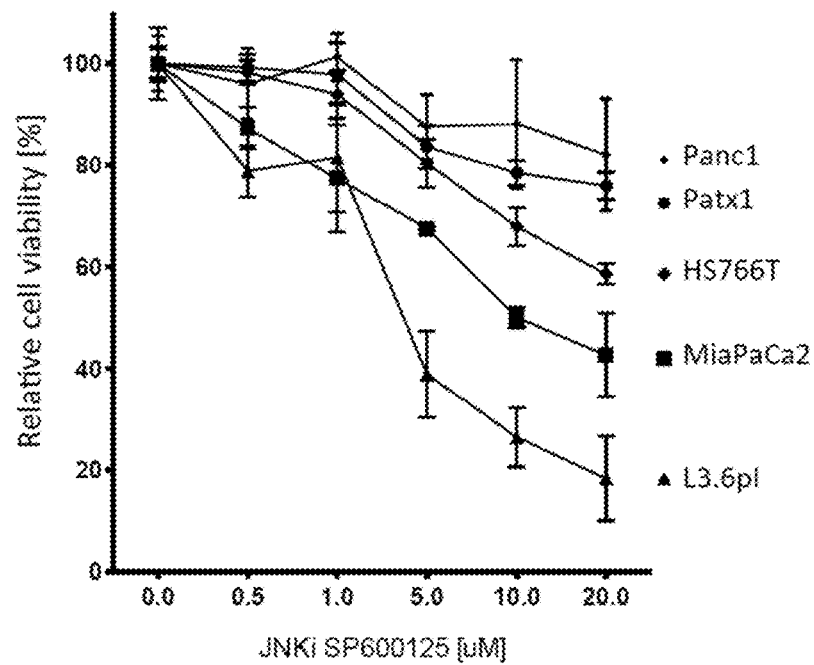

While the making and using of various embodiments of the present invention are discussed in detail below, it should be appreciated that the present invention provides many applicable inventive concepts which can be employed in a wide variety of specific contexts. The specific embodiment discussed herein are merely illustrative of specific ways to make and use the invention and do not delimit the scope of the invention.

The c-Jun N-terminal kinase (JNK) pathway is one of the pathways activated in PDAC and its transcription factor c-Jun can be induced by cellular stress, e.g., hypoxia or inflammatory signals and regulates, among other cellular processes, apoptosis. Takahashi R, et al. "Therapeutic effect of c-Jun N-terminal kinase inhibition on pancreatic cancer" *Cancer Science* 104 (2013) 337-44. Moreover, it has previously very recently shown that JNK is frequently active in PDAC downstream of oncogenic KRAS and that inactivating the JNK signaling via different mechanisms can increase apoptosis induction in some hepatocellular carcinoma cells. Davies C C, et al. "Impaired JNK Signaling Cooperates with KrasG12D Expression to Accelerate Pancreatic Ductal Adenocarcinoma" *Cancer Res.* 74 (2014) 3344.

JNK signaling also plays a critical role in regulating self-renewal and tumorigenesis in cancer stem cells (CSCs) in glioma (Yoon C-H, et al. "c-Jun N-terminal kinase has a pivotal role in the maintenance of self-renewal and tumorigenicity in glioma stem-like cells" *Oncogene* 31(44) (2012) 4655-66) and has recently been shown to maintain pancreatic CSCs downstream of mutated KRAS (Okada M, et al. "Targeting the K-Ras—JNK axis eliminates cancer stem-like cells and prevents pancreatic tumor formation" *Oncotarget.* 5(13) (2014) 5100-5112. However, heretofore, inhibition of JNK alone has proven to be of limited value in inhibiting cancer cell growth.

Many types of solid tumors have been found to be heterogeneous and to have a hierarchical organization that is driven by CSCs. CSCs exhibit remarkable abilities for self-renewal, tumorigenesis, drug resistance, and extraordinary adaptability to changing microenvironments. As such, CSCs are considered the drivers of drug-resistance and metastasis. See Todaro M, et al. "Colon Cancer Stem Cells Dictate Tumor Growth and Resist Cell Death by Production of Interleukin-4" *Cell Stem Cell.* 1 (2007) 389-402 and Lonardo E, et al. "Nodal/Activin Signaling Drives Self-Renewal and Tumorigenicity of Pancreatic Cancer Stem Cells and Provides a Target for Combined Drug Therapy" *Cell Stem Cell.* 9 (2011)433-46.

Antineoplastic strategies against bulk tumor cells as well as against tumor stem cells are imperative for successfully reducing tumor size and improving overall patient survival. This is especially crucial in cancers that are detected late in the course of the disease and in tumors that exhibit a relative drug resistance with a high propensity for metastasis. In PDAC, one further key to a successful treatment is to understand the heterogeneity of the tumor and its drivers.

As disclosed herein, we examined the role of the JNK pathway in PDAC—a pathway that is activated by inflammatory or hypoxic stimuli and is involved in apoptosis regulation.

Previous reports have suggested that JNK signaling regulates cancer stemness and presents an escape pathway to apoptosis with the majority of these data deriving from studies in hepatocellular carcinoma. Moreover, it was shown that stem-like glioma cells depend on JNK signaling, which makes this pathway an attractive target for therapeutic strategies. Interestingly, recent studies indicate that oncogenic KRAS forms a critical axis with the JNK pathway that can regulate pancreatic tumor formation.

Figure 1G:
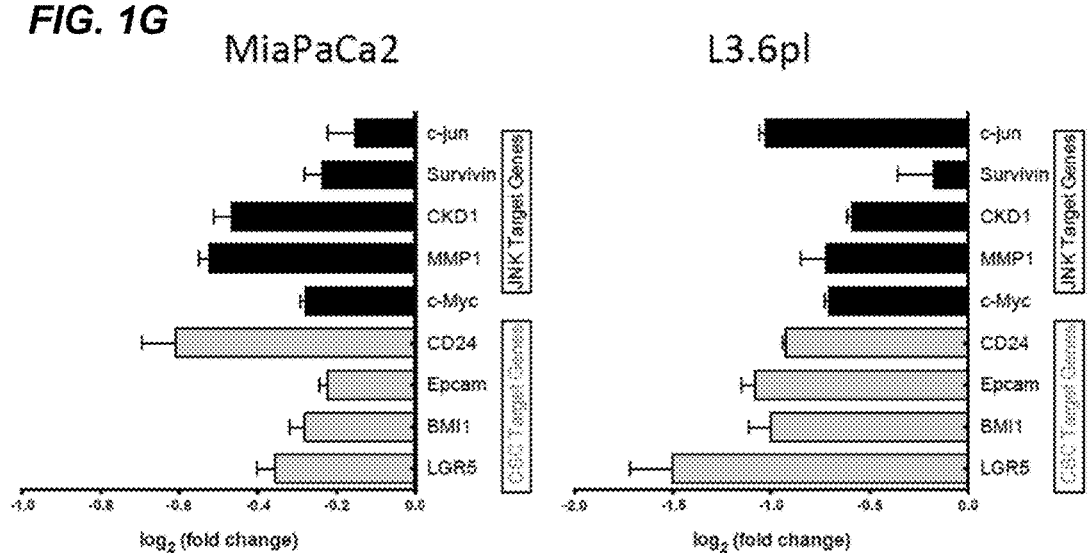
Figure 2A:
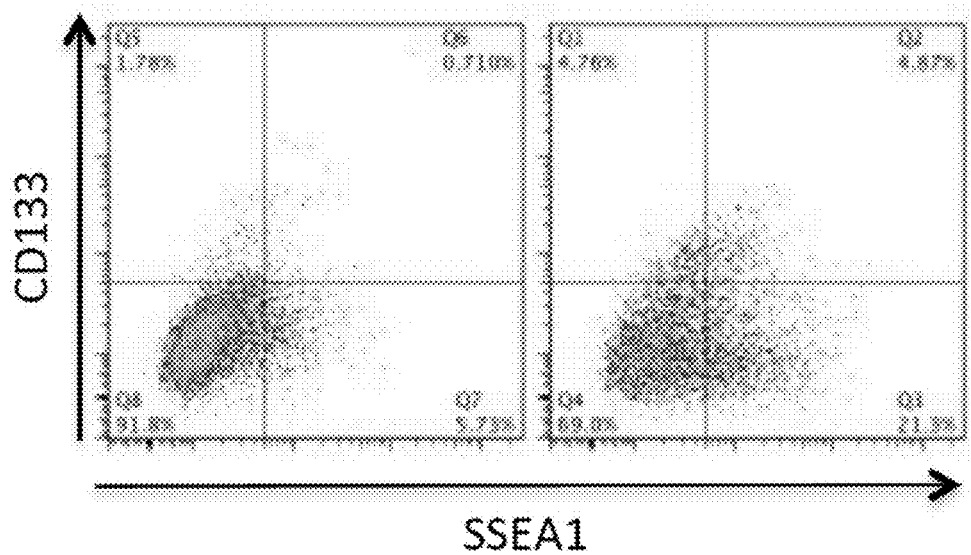
FIGS. 2A-2F demonstrate the results of experiments showing that JNK inhibition attenuates stemness potential of PDAC including by demonstrating that JNKi affects the abilities of pancreatic cancer stem cells to form spheres and reduces significantly the expression of embryonic genes in PDAC.
Figure 2B:
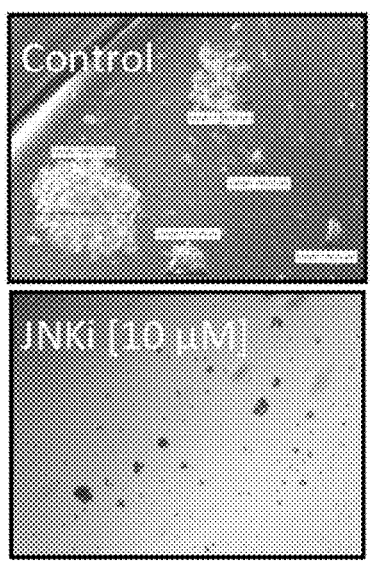
Figure 2C:
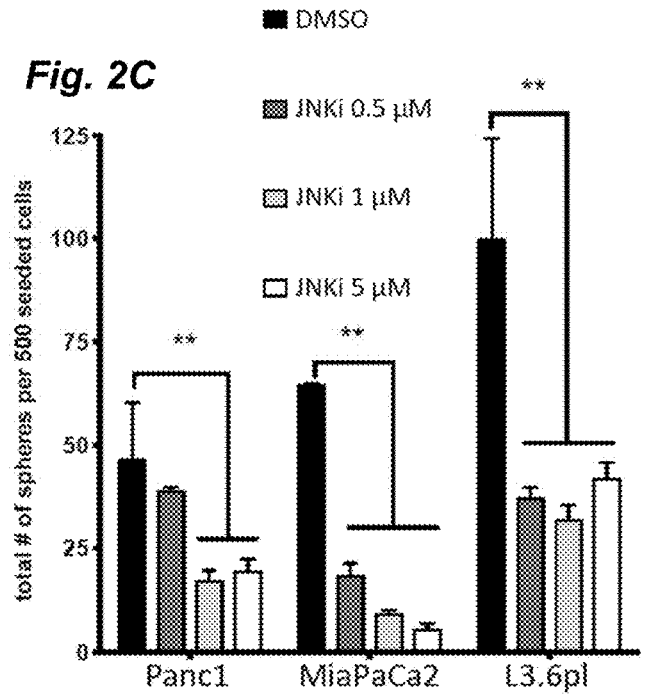
Figure 2D:
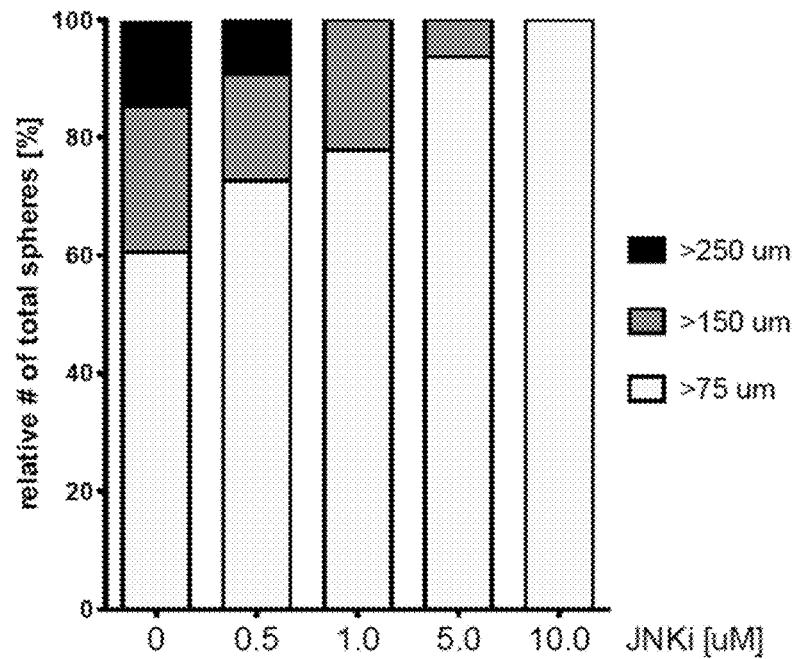
Figure 2E:
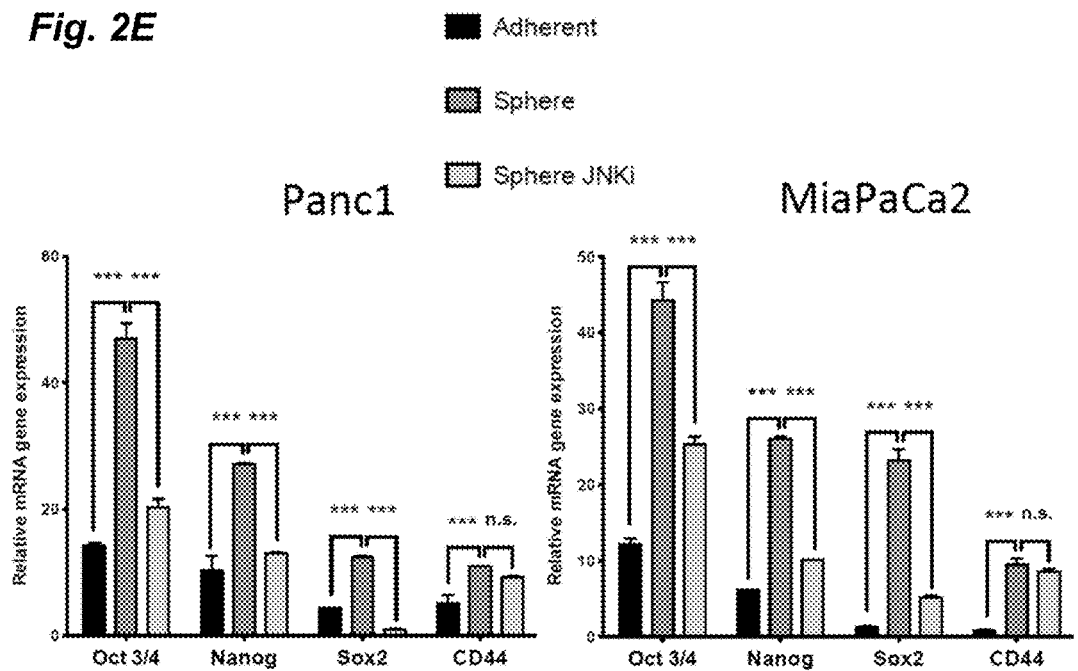

In this work, we found that low-dose JNK inhibition (JNKi) significantly decreased growth patterns in different pancreatic cancer cell lines in adherent culture (FIG. 1A, B) or nonadherent, CSC-enriched sphere culture (FIG. 2B, C, D). This suggested to us that JNK and its downstream targets are important in pancreatic cancer for proliferative activities of differentiated bulk tumor cells as well as regulation of self-renewal in pancreatic CSCs. Moreover, we found that JNKi not only reduced JNK target gene expression (FIG. 1E and FIG. 1G) but also significantly inhibited CSC markers in bulk tumor cells and in CSC-enriched spheres (FIG. 2E). The latter explains JNKi's potent effect on reducing the self-renewal capacity in CSCs.

In an attempt to potentiate JNKi's antiproliferative effect for a translational antitumor approach, we combined JNKi with a natural apoptosis-inducing substance. Here, we chose TRAIL, which is produced by many tissues and mainly induces extrinsic apoptosis in neoplastic cells because of their expression of the functional TRAIL receptors DR4 and DR5.

TRAIL (TNF-related apoptosis-inducing ligand; Apo2L; CD253; TNFSF10) is a type II transmembrane protein of about 34 kDa. As with most members of the tumor necrosis factor (TNF) superfamily of cytokines, TRAIL can be cleaved at the cell surface by metalloproteases to form a soluble molecule. Active TRAIL forms trimers and specifically binds to five distinct known receptors: TRAIL-R1 (DR4; Apo2; CD261; TNFRSF10A), TRAIL-R2 (DR5; KILLER; TRICK2A; TRICK2B; CD262; TNFRSF10B), TRAIL-R3 (DcR1; LIT; TRID; CD263; TNFRSF10C), TRAIL-R4 (DcR2; TRUNDD; CD264; TNFRSF10D), and osteoprotegerin (OPG; OCIF; TNFRSF11B).

In the case of PDAC, TRAIL-induced cell death is primarily mediated by DR4. However, many tumors also develop resistance mechanisms by upregulating intrinsic inhibitors of apoptosis, e.g. c-FLIP or the nonfunctional Decoy-TRAIL receptors DcR1 or DcR2. In hepatocellular carcinoma, it was reported that JNKi restored sensitivity to the apoptosis-inducing ligand to CD95, however only in considerably higher dosages than used in the present study.

Figure 2F:
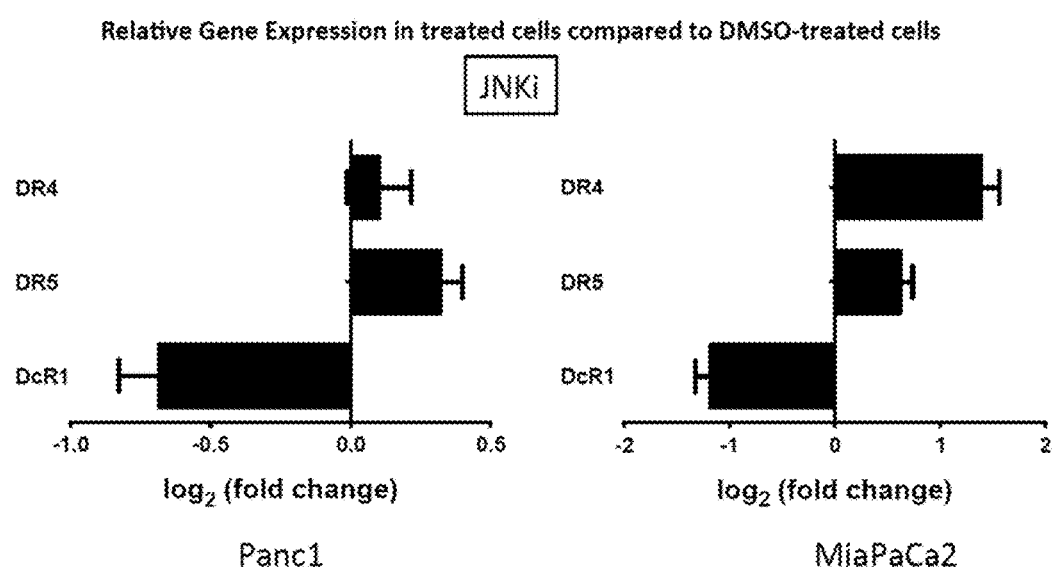
Figure 3A:
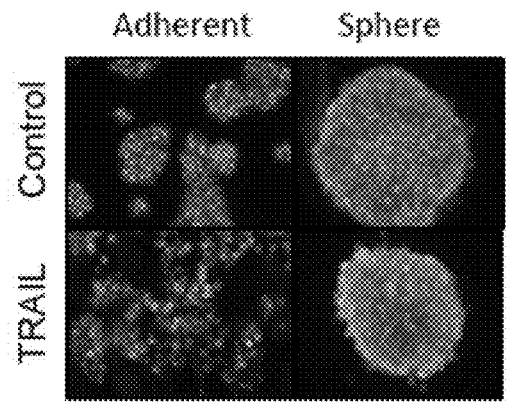
FIGS. 3A-3G demonstrate the results of experiments showing that JNKi sensitizes PDAC (CSC) to pro-apoptotic effects of TRAIL and has a significant effect on sphere formation and size.
Figure 3B:
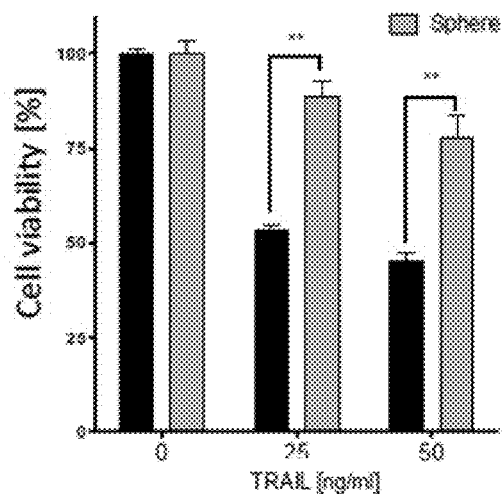

Our results demonstrate that combining low-dose JNKi and TRAIL drastically reduces cell viability in adherent, bulk tumor cells (FIG. 3C) and, to an even larger degree, in CSC-enriched spheres (FIG. 3D, E, F), which are intrinsically more resistant to TRAIL (FIG. 3A). Of note, JNKi is able to even overcome acquired TRAIL resistance in PDAC and its spheres (FIG. 4C, D, E) by upregulating the expression of functional TRAIL receptors DR4 and DR5 (FIG. 3G, 2F) and downregulating the decoy receptors DcR1 and 2.

To further test the suitability of the JNKi-TRAIL combination for possible future clinical use, we treated several orthotopic pancreatic tumors with varying TRAIL susceptibility with JNKi, TRAIL, or the combination thereof. In an animal model of orthotopic xenografts, tumors were treated successfully with very low doses of TRAIL (FIG. 6). Only in one cell line (MiaPaCa2), the low doses of both, JNKi and TRAIL, were not able to significantly impact on in vivo tumor growth.

Importantly, we found a reduction in metastatic spread indicative of a significant anti-cancer stem cell effect of this combination in vivo (Table 1). Furthermore, we demonstrate that JNKi, TRAIL, and the combination of these two agents in doses up to five times of those used in our in vivo treatment have no effect on proliferation, survival, and, most importantly, the functional differentiation capacity of normal tissue-resident stem cells (FIGS. 8A-D). This indicates that the concept of JNKi/TRAIL combination treatment could be clinically well tolerated by pancreatic cancer patients. Moreover, even under hypoxic conditions, which are typically found in poorly vascularized cancers such as PDAC and which also activate stress pathways, adult ASCs remained unaffected by JNKi and TRAIL. In contrast, PDAC tumor cell lines showed significant levels of cell death including TRAIL-resistant tumor cell lines.

Figure 6A:
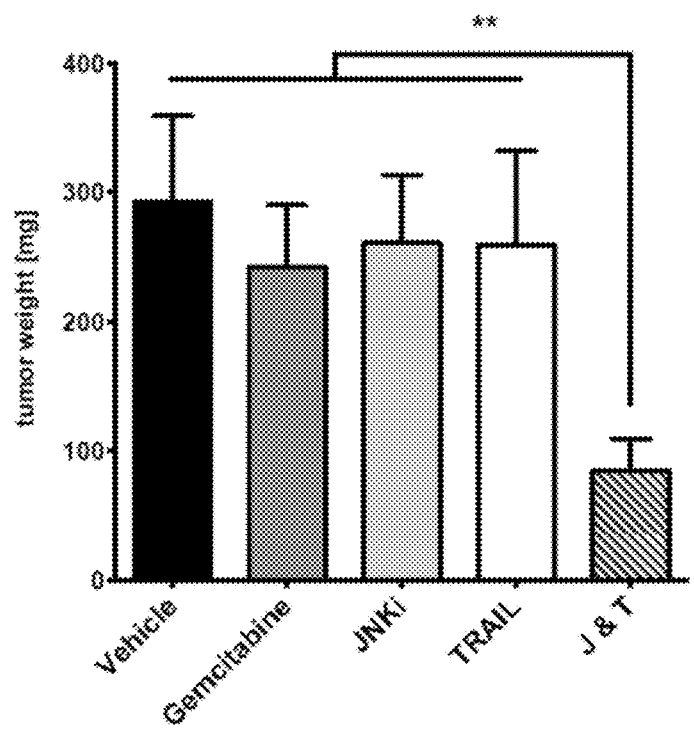
FIGS. 6A-6F demonstrate the results of experiments showing the effects of JNKi and TRAIL in orthotopic in vivo models.
Figure 6B:
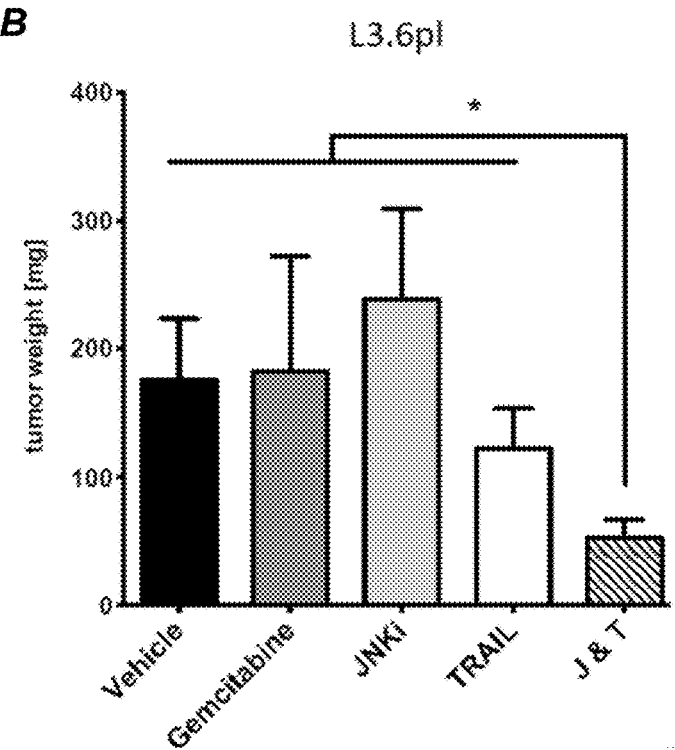
Figure 6C:
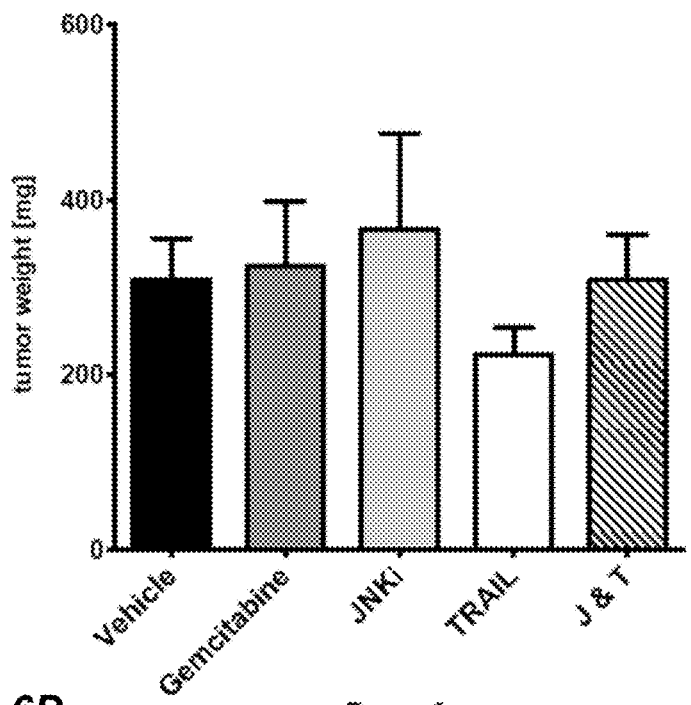
Figure 6D:
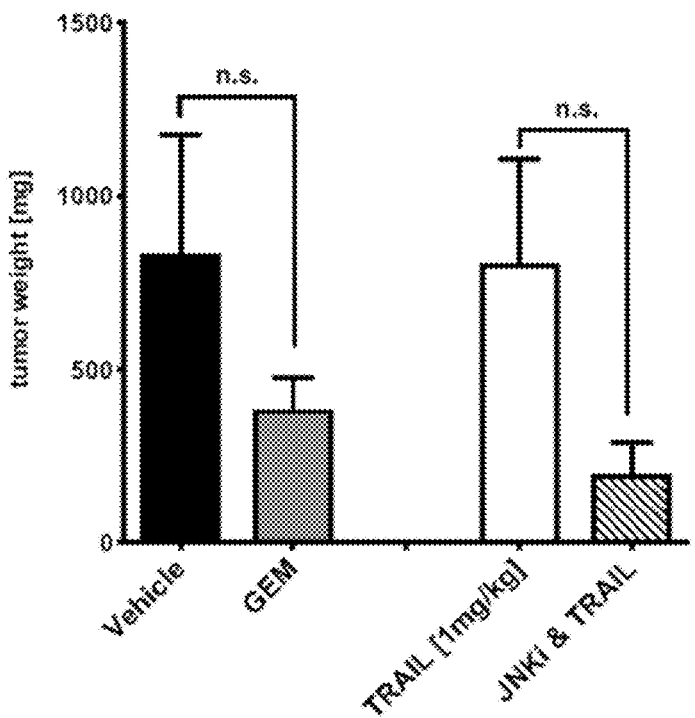

Recent biomarker profiling of pancreatic cancer suggests that functional p38 MAPK activity inhibits JNK and thus improves overall survival, thus corroborating our approach. However, this report did not characterize the missing link between the different pathways. Here, we identified IL-8 as the critical link between the JNK pathway, TRAIL resistance, and cancer stemness in PDAC. It was previously shown that IL-8 and its receptor CXCR1 are protagonists especially in breast cancer stem cells. Moreover, in a prostate cancer model, Wilson et al. showed that endogenous IL-8 or drug-induced heightened secretion of IL-8 substantially reduced drug sensitivity and, in a similar manner, IL-8 treatment was shown to induce relative TRAIL-resistance in the ovarian cancer cell line OVCAR3. As disclosed herein, we show that TRAIL-induced IL-8 secretion improved cell survival by increasing the expression of TRAIL-decoy receptors DcR1 and 2 and reducing death receptors DR4 and 5 when facing TRAIL; the latter effects were reversible by JNKi (FIG. 6A, B). In turn, blocking of IL-8 signaling by antibodies against IL-8 or its receptor CXCR1 reduced survival and cancer stemness significantly (FIG. 6B, C). JNKi interfered with this axis to some extent by decreasing CXCR1 expression (FIG. 6D).

In summary, our findings show for the first time that the JNK pathway is an important CSC-regulatory pathway in pancreatic cancer. Its inhibition offers a selective novel approach to treat pancreatic cancer by targeting parental pancreatic cancer cells and, to an even higher degree, affecting the growth and physiology of pancreatic cancer stem cells. Most importantly, we provide evidence from our experiments that this combined sensitizing treatment has a considerable safety window, as the physiology of normal tissue-resident stem cell is not impacted, even at much higher drug doses as used in the animal study.

In one embodiment disclosed herein, we administered TRAIL systemically by intraperitoneal injections. However, it is known that an increase in systemic levels of TRAIL can be associated with side effects. Previous studies have shown that stem cells home to tumor sites described as a "never healing wound" after i.v. application. Hence, in other embodiments genetically modified mesenchymal stem cells that overexpress TRAIL would be employed to selectively increase local TRAIL levels in the tumor environment. In other embodiments, the TRAIL delivered by genetically modified mesenchymal stem cells is combined with systemically applied low-dose JNK inhibition. The approach we describe is representative of the next generation of cancer therapy as it aims to be a more selective, targeted, efficacious and possibly safer mode of treatment.

The following examples are included for the sake of completeness of disclosure and to illustrate the methods of making the compositions and composites of the present invention as well as to present certain characteristics of the compositions. In no way are these examples intended to limit the scope or teaching of this disclosure.

Example 1: Combination of JNKi and TRAIL for Reducing Tumor Growth

PDAC Depends on JNK Signaling for Growth and Survival:

JNK is a stress-responsive kinase that is involved in apoptosis, tumorigenesis, and other signaling events. To understand the role and mechanisms of JNK in PDAC, we treated five different well-characterized pancreatic cancer cell lines with increasing concentrations of the anthrapyrazolone JNK inhibitor SP600125 (Bennett B L, et al. SP600125, an anthrapyrazolone inhibitor of Jun N-terminal kinase. *Proc Natl Acad Sci USA*. 98 (2001) 13681-6.) for 24 hours. Low-dose treatment (0.5 µM or 1.0 µM) resulted in negligible effect on cell viability in Panc1, Patx1, and HS766T cells and an 80% cell viability in MiaPaCa2 and L3.6pl cells (FIG. 1A). As used herein, the term "low-dose JNKi" means doses of a JNKi at or below 1.0 µM. But how do we translate this to in vivo doses.

Figure 1B:
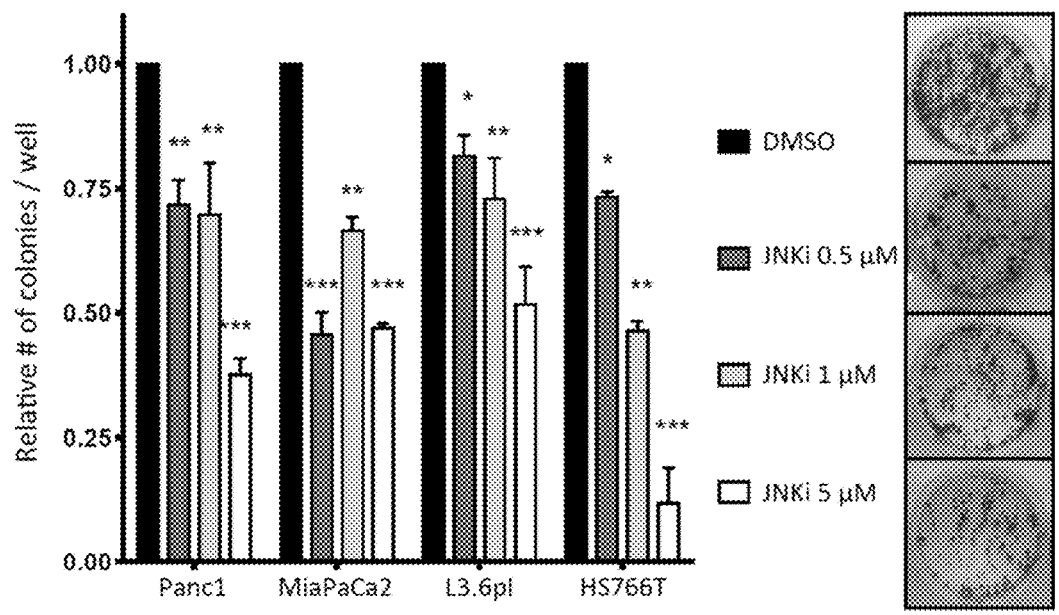

High-dose treatment (5.0 µM, 10.0 µM, or 20.0 µM) resulted in markedly decreased cell viability in all five cell lines. Next, we determined the effects of JNKi on clonogenic growth behavior with colony-forming assays. Quantitative analysis after 10 days revealed a dose-dependent inhibition of both the number of colonies formed in all cell lines (FIG. 1B, left side) and reduction in size of colonies (FIG. 1B, right side e.g. MiaPaCa2).

Figure 1F:
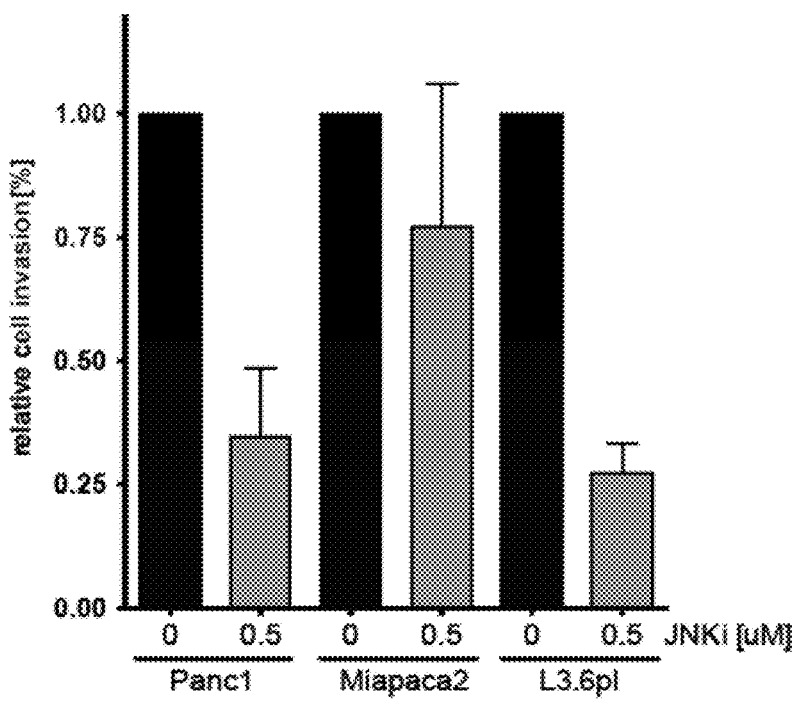

Because JNKs are involved in stress-induced processes, we performed wound healing assays by scratching a 2-D monolayer of pancreatic cancer cells. Close to the scratch margins, activated phospho-c-Jun, a downstream member of the JNK pathway, was shown to be activated after 24 h. JNKi inhibited wound closure in a dose-dependent manner (FIG. 1C) as well as phosphorylation of c-Jun. Of note, for up to 32 hours, JNKi even at low doses had significant effects on wound healing (FIG. 1D). Furthermore, low-dose JNKi (0.5 µM) substantially inhibited invasive behavior of Panc1 and L3.6pl cells in a three-dimensional matrigel-coated Boyden invasion chamber assay (FIG. 1F). For the data presented in FIG. 1F, the relative invasion of Panc1, MiaPaCa2, and L3.6pl cells were counted in four different view fields and presented as the mean±SD.

Finally, to shed light on the mechanistic background, we performed qRT-PCR on established JNK target genes, including c-Jun, Survivin, CKD1, MMP1, and c-Myc, in untreated and low-dose JNKi-treated pancreatic cancer cells. As expected, JNK target genes (cJun, Survivin, CKD1, MMP1, c-Myc) were significantly downregulated after JNKi treatment (FIG. 1E and FIG. 1G). As shown in FIG. 1G, CSC target genes (CD24, EpCAM, BMI1, and LGR5) were also downregulated after JNKi treatment, suggesting that the JNK pathway might play a role in the regulation of CSC in pancreatic cancer. In FIG. 1G, expression of JNK target genes (black bars) or CSC target genes (grey bars) in JNKi-treated cells (0.5 µM) is shown relative to expression in untreated cells as determined by qRT-PCR. Values of genes were standardized to the respective values of housekeeping genes.

JNK Inhibition Attenuates Stemness Potential of PDAC:

Since JNKi seemed to inhibit known CSC target genes, we investigated the role of JNK in pancreatic cancer stemness in more detail. One accepted model for enriching cells exhibiting CSC characteristics is tumorsphere culture. In line with previous reports, we found that pancreatic cancer sphere cells were highly enriched in stem cell markers such as CD133 and SSEA1 (FIG. 2A).

Sphere-forming ability is often used as a quantitative estimate of the number of CSCs within a tumor cell population. Similar to how JNKi reduced colony formation, JNKi even at low concentrations of 0.5 µM significantly reduced the number of spheres (FIG. 2C). Moreover, in all cell lines analyzed, JNKi drastically reduced sphere size (FIG. 2B). Of note, JNKi exhibited a dose-dependent impact on relative sphere sizes: 40% of spheres in the control group were bigger than 150 µm in diameter, compared to 0% in the high-dose treatment group (FIG. 2D).

To further understand the effects of JNKi on cancer stemness, we carried out qRT-PCR on CSC markers Oct3/4, Nanog, Sox2, and CD44. As expected, we found that expression of these CSC markers was significantly higher in spheres compared to parental cancer cells (FIG. 2E). However, low-dose JNKi decreased the expression of these CSC markers to levels closer to those detected in parental cells, suggesting that JNKi-treated cells partially lose their CSC phenotype in sphere culture. FIG. 2F shows gene expression of DR4, DR5, and DcR1 in Panc1 and MiaPaCa2 cells after treatment with JNKi for 24 hours. Shown are the relative values compared to untreated controls. The experiment was performed in triplicate.

JNKi Sensitizes PDAC Cells and CSCs to the Pro-Apoptotic Effects of TRAIL:

TRAIL is a subject of excitement in the field of cancer therapy. Cancer cells exhibit increased expression of the TRAIL receptors, death receptors DR4 and DR5. Thus, TRAIL is a natural apoptosis inducer with a preferential effect on cancer cells (Lemke J, et al. "TRAIL signaling is mediated by DR4 in pancreatic tumor cells despite the expression of functional DR5" *J Mol Med.* 88 (2010) 729-40). We first investigated whether CSC-enriched pancreatic cancer spheres are susceptible to TRAIL. To do so, we used the acridine orange/ethidium bromide staining. In L3.6pl cells, parental cells treated with 50 ng/mL TRAIL demonstrated robust apoptosis at 24 hours (FIG. 3A, lower left), whereas spheres treated with the same regimen were almost entirely viable (FIG. 3A, lower right). MTT viability assay showed that spheres were significantly more resistant to TRAIL-induced cell death than were parental cells at both TRAIL concentrations tested: 25 ng/mL and 50 ng/mL (FIG. 3B) highlighting the important role of cancer stem cells as drivers of tumor growth and resistance to treatment. As used herein, low dose TRAIL means at or less than 25 ng/ml.

Figure 3C:
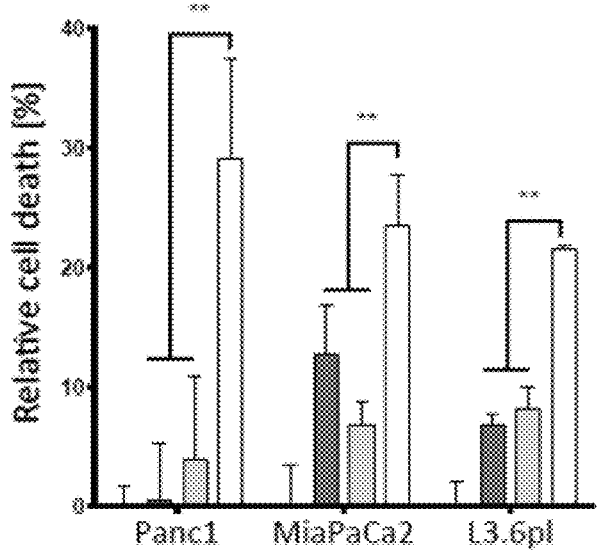

MTT cell viability assays showed that low-dose JNKi (0.5 µM) alone and low-dose rhTRAIL (in this case 10 ng/mL) alone exerted only modest effects on cell viability in parental pancreatic cancer cells (FIG. 3C). Since we had observed a substantial reduction of stemness potential following treatment with JNKi, we studied the effects of combining JNKi treatment with TRAIL treatment. We expect that this dosage would be clinically achievable and tolerable with no or little side effects. The combination of JNKi and TRAIL induced a surprisingly robust reduction in cell viability in all three cancer cell lines tested: Panc1, MiaPaCa2, and L3.6pl (FIG. 3C).

Figure 3D:
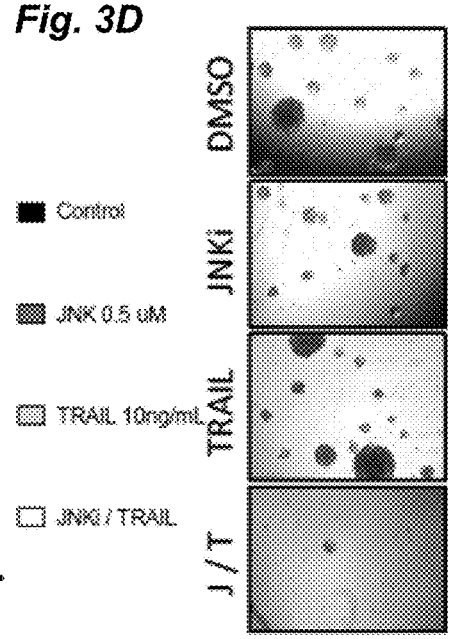
Figure 3E:
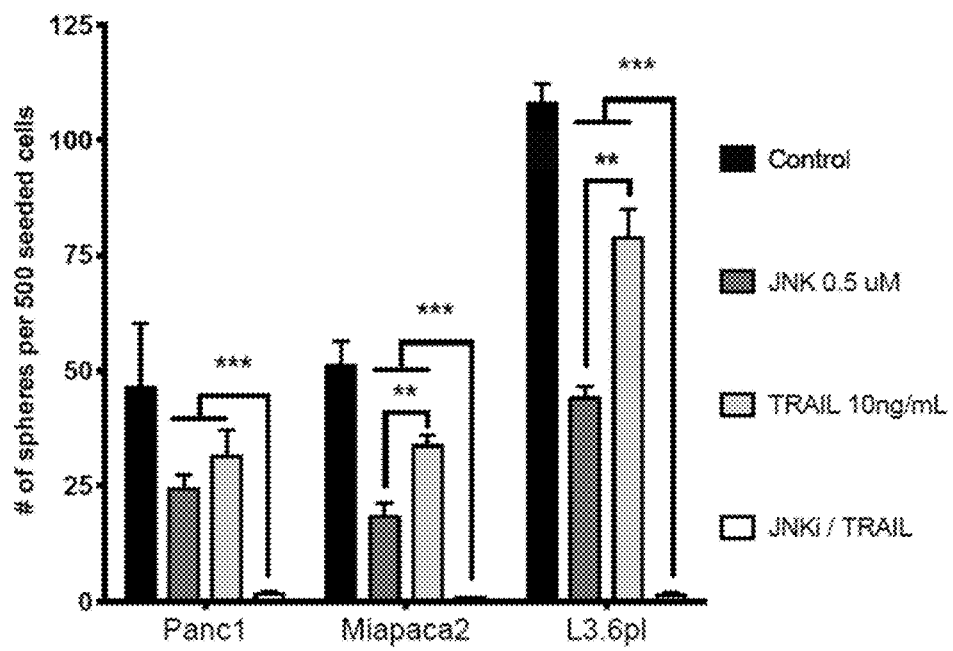
Figure 3F:
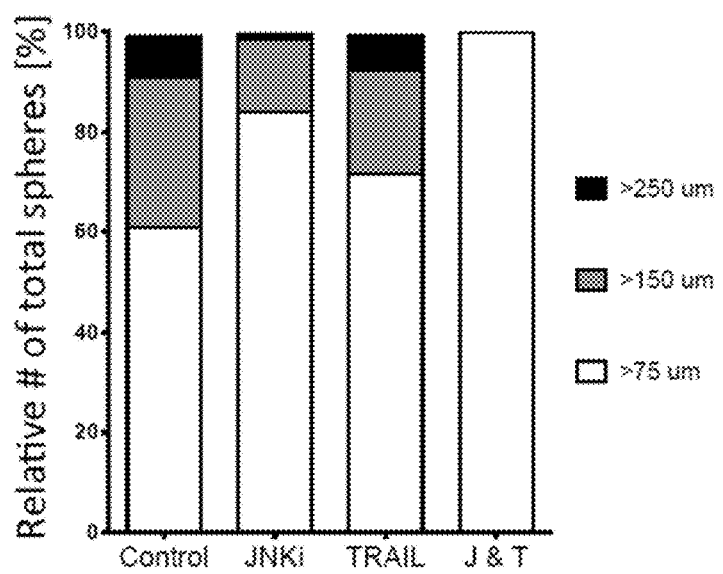
Figure 3G:
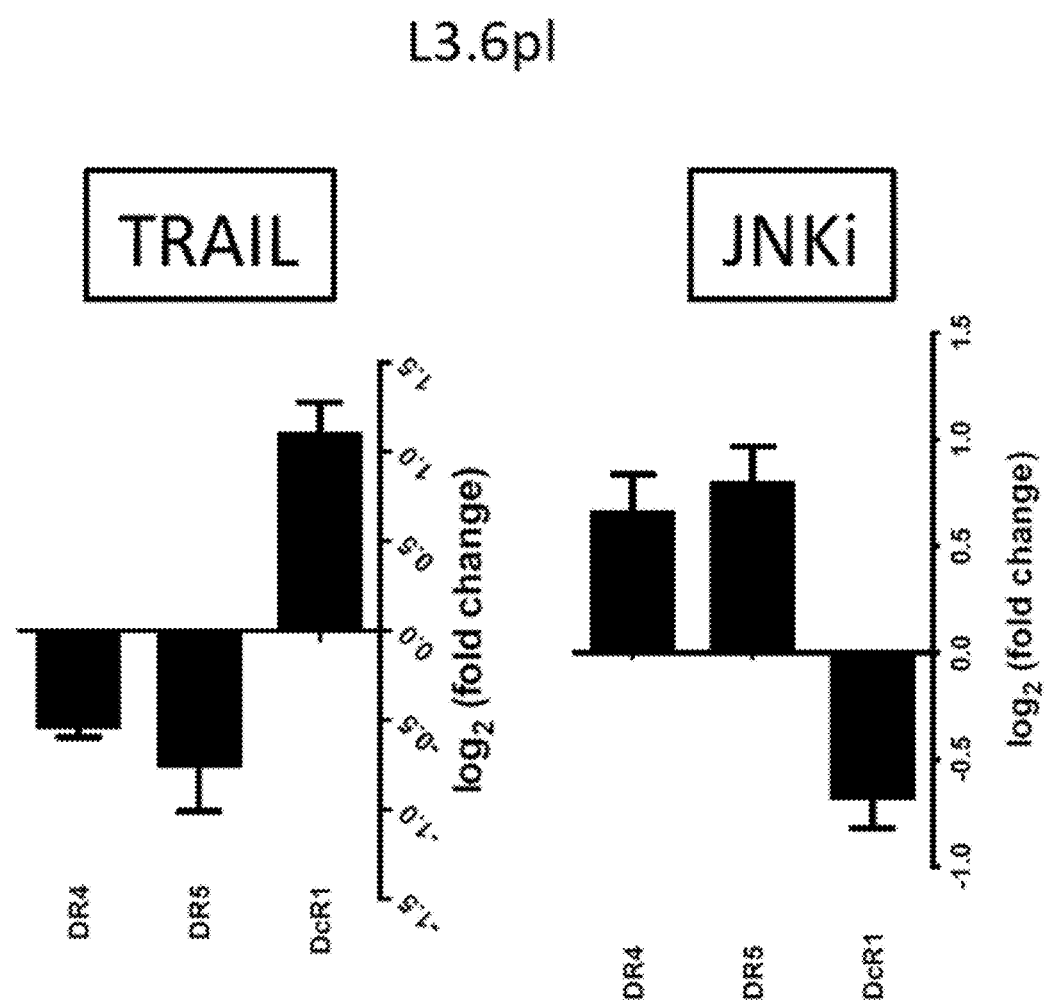

We extended our experiment to CSC-enriched spheres and found that JNKi alone reduced sphere size to some extent, as expected, but that the combination of JNKi and TRAIL completely inhibited sphere growth (FIG. 3D). Quantification of the total sphere number showed that the low-dose combination of JNKi and TRAIL significantly reduced the total number of spheres to a minimum (FIG. 3E). Relative quantification of the sphere sizes showed that treatment with the combination of JNKi and TRAIL only allowed growth of the smallest spheres (>75 µm) (FIG. 3F) suggesting a substantial inhibition of CSC proliferation.

Mechanistically, we found by qRT-PCR that TRAIL treatment alone reduced the presence of the apoptosis receptors DR4 and DR5 compared to control samples (FIG. 3G, left panel) and increased the expression of the decoy receptor DcR1. This suggests that TRAIL-resistance of CSCs is based on increased expression of the decoy receptor DcR1 effecting increased survival after TRAIL treatment, because binding of TRAIL to DcR1 does not result in apoptosis induction. In contrast, treatment with JNKi reversed that phenomenon by increasing the expression of TRAIL death receptors DR4 and DR5 and reducing expression of the TRAIL decoy receptor DcR1 (FIG. 3G, right panel, and FIG. 2F); thus, enabling TRAIL to induce apoptosis in the CSC and explaining the sensitization of CSCs to TRAIL therapy.

Figure 4A:
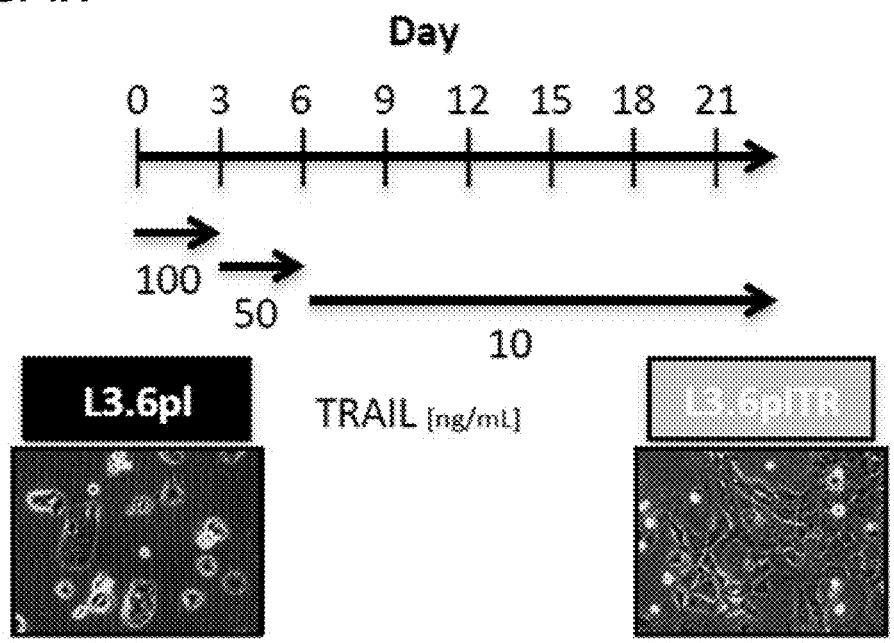
FIGS. 4A-4F demonstrate the results of experiments showing that PDAC cells with acquired TRAIL-resistance can be resensitized by JNK treatment to TRAIL-induced apoptosis.
Figure 4B:
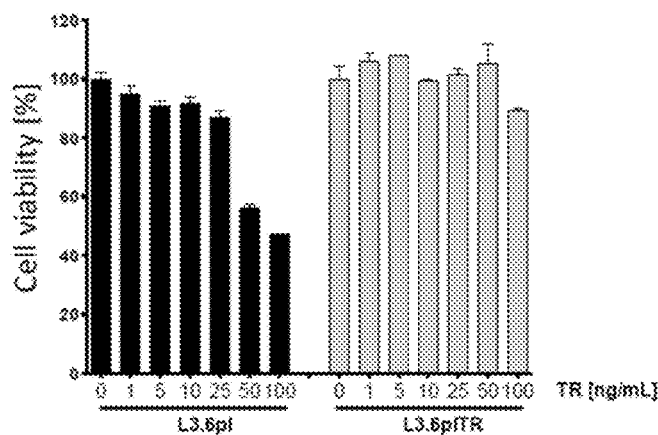

Even PDAC Cells with Acquired TRAIL Resistance can be Resensitized by JNK Treatment to TRAIL-Induced Apoptosis:

To mimic the TRAIL-resistant behavior of CSCs, we artificially created a TRAIL-resistant cell line from parental L3.6pl cells, which are highly sensitive to TRAIL. The regimen for inducing TRAIL resistance is described schematically in FIG. 4A. Morphologically, cells changed from an epithelial phenotype (FIG. 4A, left) to a mesenchymal phenotype (FIG. 4B, right) similar to that observed in Panc1, a TRAIL-resistant cell line. Compared to parental cells, TRAIL-resistant L3.6pl cells (L3.6plTR) were more resistant to TRAIL and showed detectable cell death only in small numbers of cells, even at TRAIL doses up to 100 ng/mL (FIG. 4B).

Figure 4C:
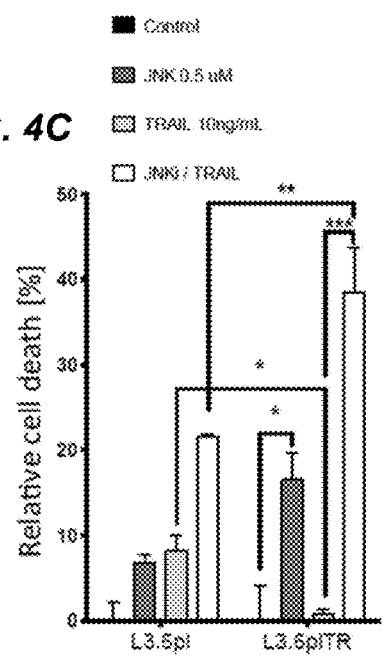
Figure 4D:
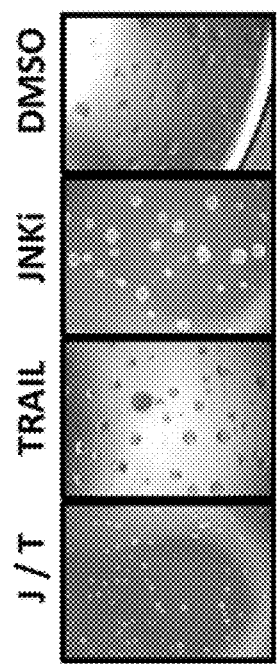
Figure 4E:
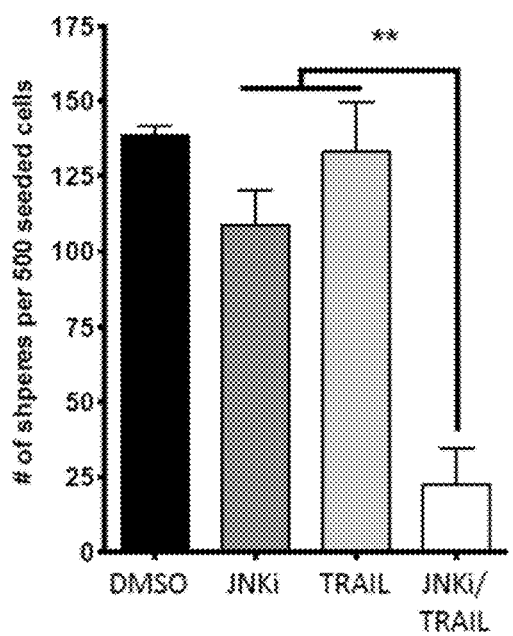
Figure 4E:
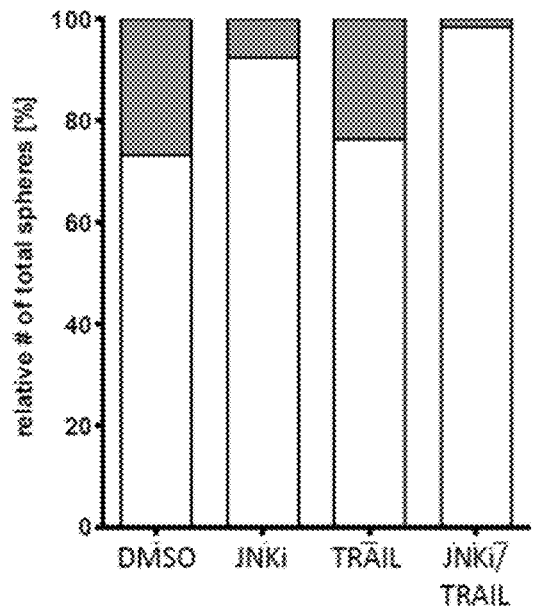

Next, we investigated the effect of our established regimen of low-dose JNKi and TRAIL on L3.6plTR cells. JNKi significantly reduced cell viability in L3.6plTR cells, and to our surprise, the combination of JNKi with TRAIL induced cell death in up to 40% of cells, a significantly greater percentage than observed with JNKi-TRAIL treatment in the parental L3.6pl cell line (FIG. 4C). As with TRAIL-sensitive L3.6pl spheres, we observed that CSC-enriched L3.6plTR spheres were highly susceptible to the combination of JNKi and TRAIL with respect to both sphere size (FIG. 4D) and total sphere number (FIG. 4E, left panel). With JNKi treatment and even more with the combination treatment, almost all of the spheres formed were smaller than 75 μm in diameter (FIG. 4E, right panel).

Figure 4F:
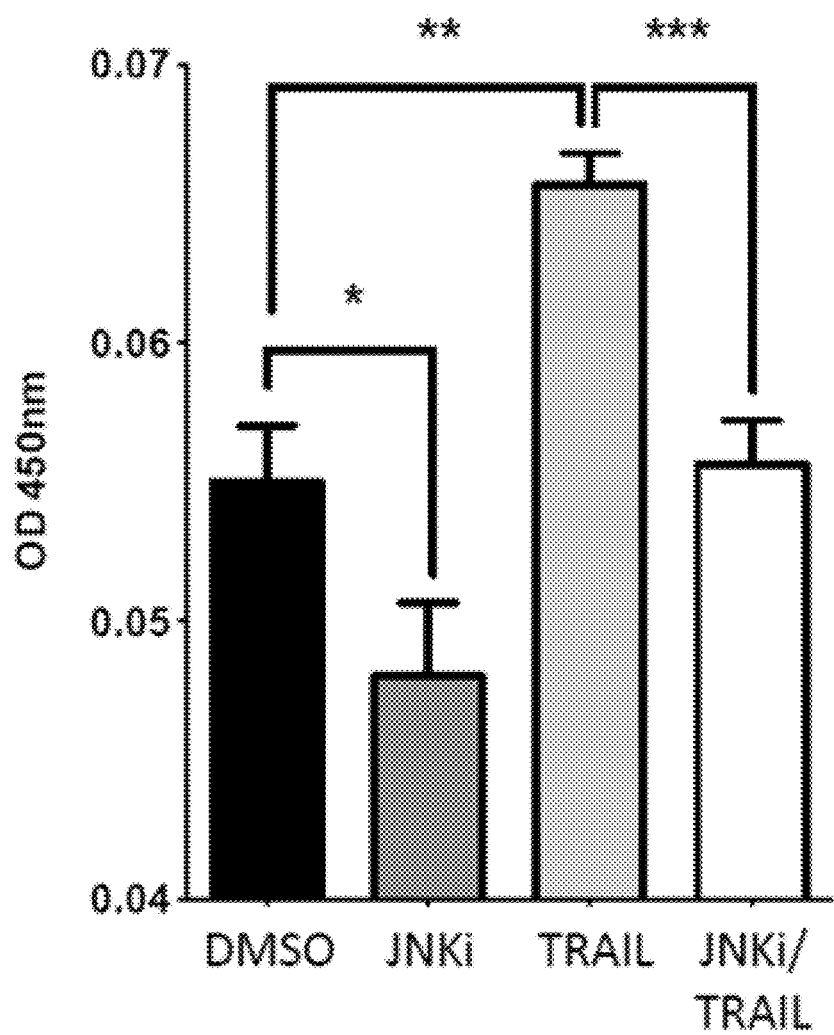

Sandwich ELISA of p-JNK revealed that JNKi treatment reduced p-JNK expression and TRAIL treatment resulted in increased p-JNK levels in L3.6plTR cells compared to untreated control cells (FIG. 4F). The combination of JNKi and TRAIL blocked this increase, presumably blocking an important apoptosis escape mechanism of TRAIL-resistant cells.

JNKi does not affect physiology and function of normal tissue-resident stem cells: Currently available cancer treatment regimens often have a limited effect especially on cancer stem cells but affect normal rapidly growing and dividing cells in the intestinal epithelium and on regular adult tissue-resident stem cells to a degree that prevents an increase in dosage. To pre-clinically test whether our approach would be later associated with possible clinically relevant side effects, we isolated human adipose tissue-derived stem cells (ASCs) as reported before (Bai X, et al. "Both cultured and freshly isolated adipose tissue-derived stem cells enhance cardiac function after acute myocardial infarction" *Eur Heart J.* 31 (2010) 489-501) in a first step and subjected them to increasing doses of JNKi. Proliferation was only affected at unphysiologically high doses of 10.0 μM or 20.0 μM, and, even then, cell proliferative capacity was only 20% lower compared to untreated ASCs (FIG. 8A).

To understand whether and how the combination of JNKi and TRAIL would affect cell survival, we treated ASCs with doses of JNKi and TRAIL up to five times of those used in low-dose pancreatic cancer treatment regimens. We found no differences in cell survival compared to control cells (FIG. 8B). Most importantly, ASCs were functionally unimpaired by JNKi, TRAIL, or the combination as determined by differentiation assays along the mesodermal lineage into osteoblasts (FIG. 8C, upper panel, Alizarin Red), chondrocytes (middle panel, Alcian Blue), or adipocytes (lower panel, Oil Red O), suggesting that adult stem cells are unaffected in their cell physiology and multipotent differentiation potential by the single treatment or the combination JNKi and TRAIL.

Because the microenvironment of pancreatic cancers is very desmoplastic, tumors tend to be hypoxic. To simulate these conditions, we cultured the pancreatic cancer cells L3.6pl and L3.6plTR as well as hASCs under hypoxic conditions and evaluated their response to DMSO, JNKi, TRAIL, or a combination thereof after 48 h. Of note, hASCs were completely unaffected, whereas 60% of L3.6pl and 40% of L3.6plTR could be detected as early or late apoptotic by Annexin V-FITC/PI staining (FIG. 8D-G). The selective increased apoptosis induction in cancer stem cells and the absence of effects on regular normal tissue resident stem cells is with regard to avoidance of potential later side effects an important finding for an intended clinical application.

Figure 5A:
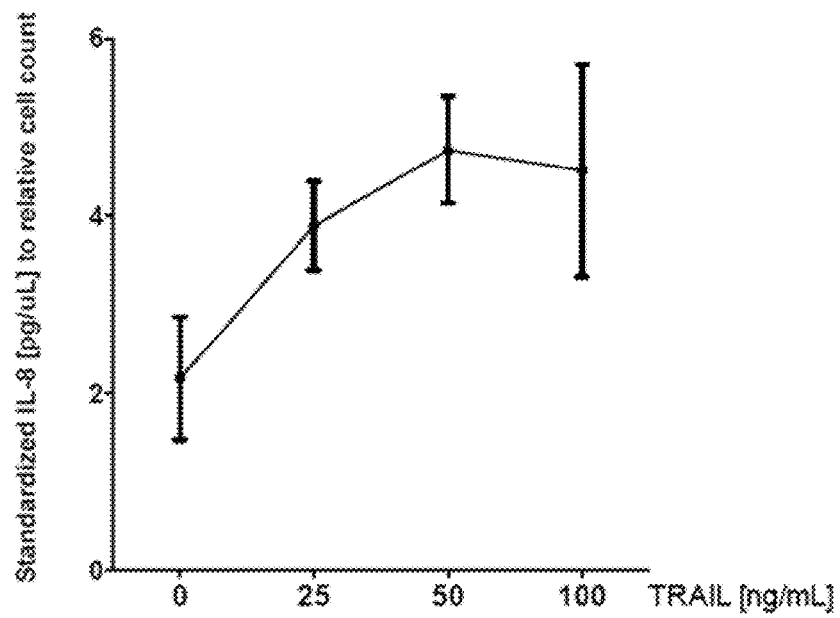
FIGS. 5A-5F demonstrate the results of experiments showing that TRAIL-resistance is mediated by autocrine IL-8 downstream of JNK.
Figure 5B:
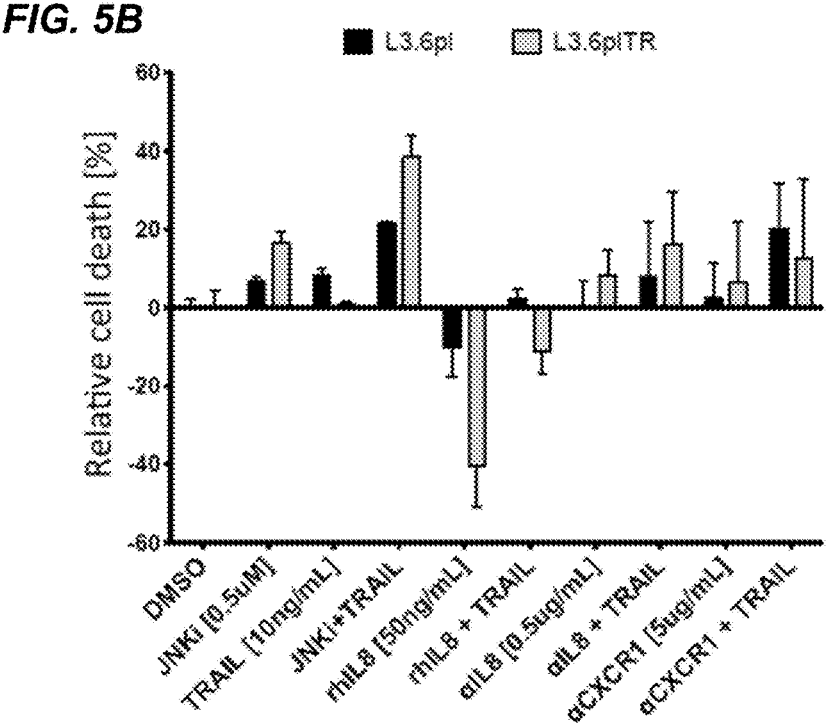
Figure 5C:
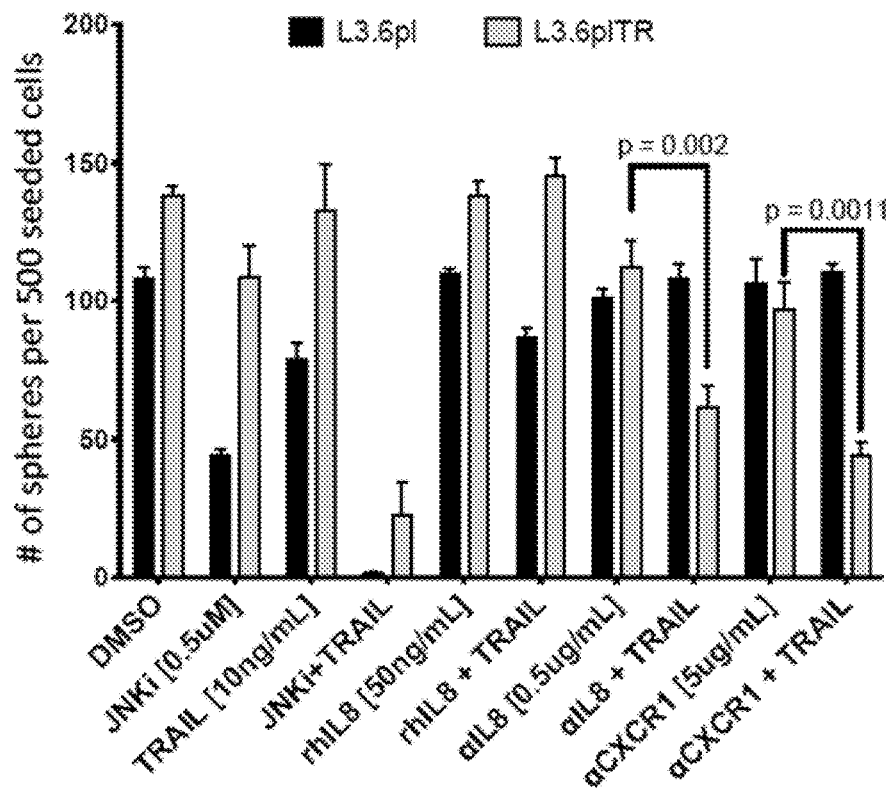
Figure 5D:
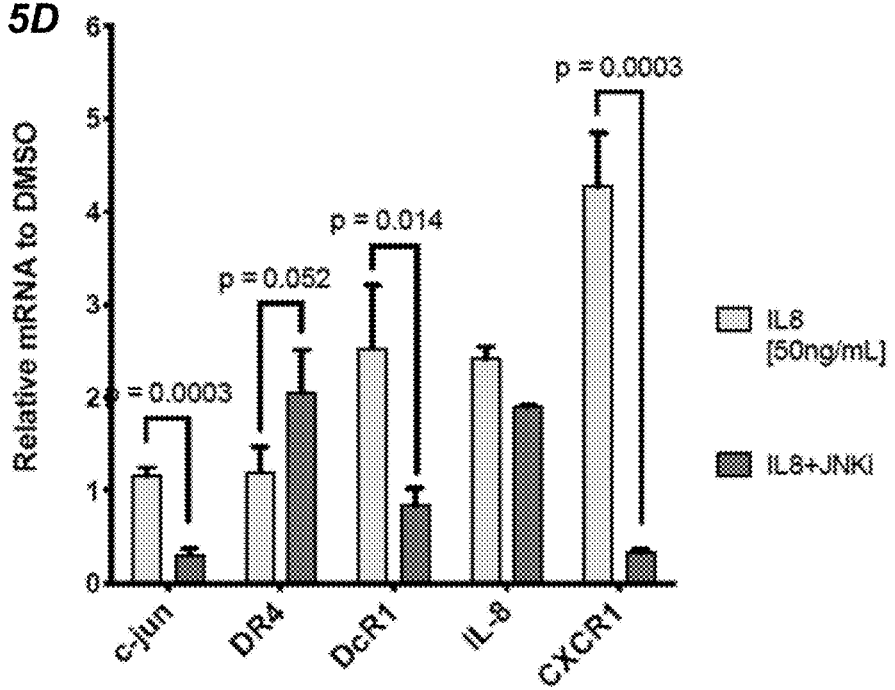
Figure 5E:
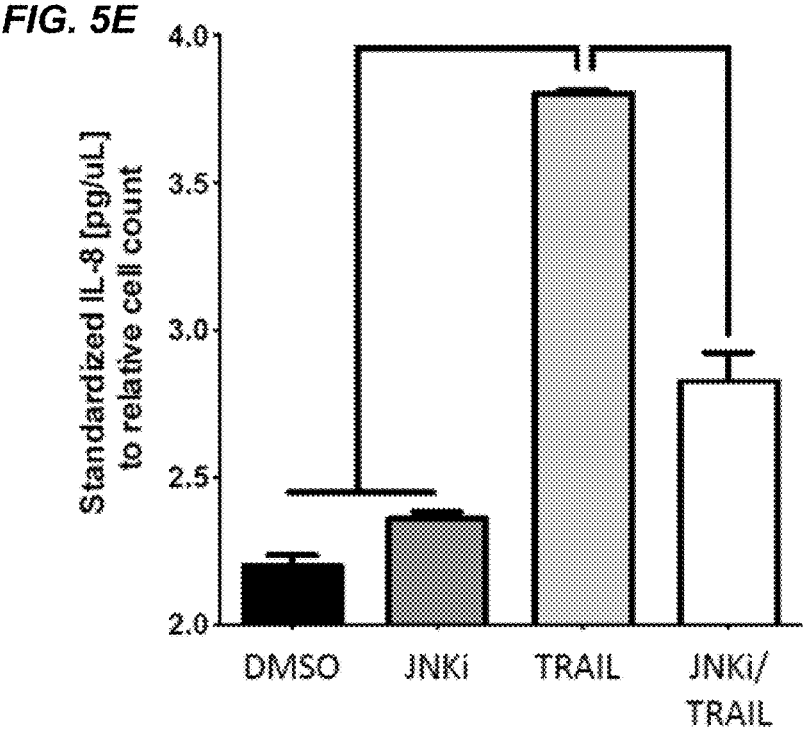

TRAIL Resistance is Mediated by Autocrine IL-8 Downstream of JNK:

After establishing the critical role of JNK for pancreatic cancer stem cells, we tried to better understand the underlying molecular connection between JNK activation and TRAIL resistance. IL-8 was reported to attenuate TRAIL sensitivity by upregulating the endogenous Caspase-8 inhibitor cFLIP in prostate cancer cells (Wilson C, et al. "Interleukin-8 signaling attenuates TRAIL- and chemotherapy-induced apoptosis through transcriptional regulation of c-FLIP in prostate cancer cells" *Mol Cancer Ther.* 7 (2008) 2649-61). We treated pancreatic cancer cells with increasing doses of TRAIL for 24 hours and determined the IL-8 secretion by ELISA (FIG. 5A). The IL-8 production increased dose-dependently and exhibited a peak secretion at sublethal TRAIL levels (50 ng/mL in Panc1 cells). Next, we explored whether addition of IL-8 or blocking of IL-8 signaling by antibodies against either IL-8 (aIL-8) or its receptor CXCR1 (αCXCR1) in combination with TRAIL influenced cell viability. Cell viability analysis showed that IL-8 treatment neutralized the apoptosis-inducing power of TRAIL in L3.6pl cells and even more in L3.6plTR cells (FIG. 5B). Conversely, blocking of CXCR1 or IL-8 in combination with TRAIL showed encouraging synergetic apoptosis effects compared to TRAIL alone, especially in L3.6plTR cells (FIG. 5B, right). We also tested the effect of the combinations on sphere-forming assays and found that L3.6plTR cells were particularly sensitive to blocking of IL-8 signaling in combination with TRAIL (FIG. 5C, right). Quantitative RT-PCR revealed that IL-8 autostimulated IL-8 and CXCR1 expression and contributed to TRAIL resistance by upregulation of the decoy receptor DcR1 (FIG. 5D). JNKi downregulated c-Jun and DcR1 as expected and, surprisingly, lowered CXCR1 levels considerably (FIG. 5D), suggesting cross-links on multiple levels of these pathways. Finally, we confirmed by ELISA that TRAIL upregulates IL-8 secretion through JNK signaling and that IL-8 secretion can be blocked by JNKi (FIG. 5E).

Figure 5F:
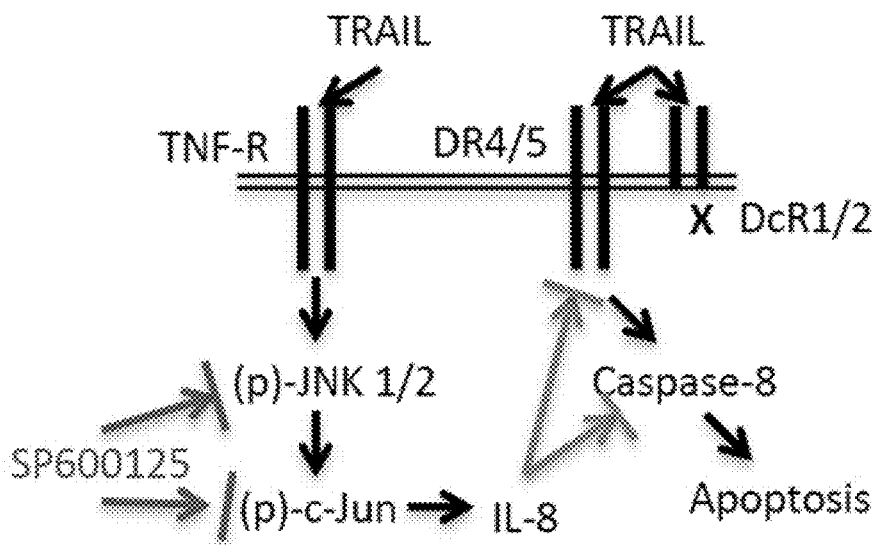

Together, our findings suggest the following model graphically summarized in FIG. 5F: Pancreatic CSCs escape TRAIL-induced apoptosis through activation of JNK signaling, which, in turn leads to increased IL-8 secretion and TRAIL resistance through downregulation of DR4/DR5 and upregulation of DcR1. IL-8 induces the expression of its cell surface receptor CXCR1 resulting in an autocrine feedback loop. This could presumably maintain TRAIL-resistance in pancreatic CSCs. On the other hand, these loops could be disrupted at multiple levels by JNKi (SP600125), αIL-8, or αCXCR1, restoring the TRAIL-sensitive pancreatic cancer subtype.

Combination of JNKi and TRAIL Reduces Tumor Growth In Vivo:

To mimic the clinical situation where physicians face different pancreatic tumors in different patients, we considered all tumors studies explained later in the text in a cluster analysis. We found that JNKi/TRAIL treatment significantly reduced tumor weight over different subtypes compared with treatment with TRAIL alone, JNKi alone, or gemcitabine or control (FIG. 6A). To test the efficacy of the combination of JNKi and TRAIL in vivo, we injected L3.6pl or MiaPaCa2 pancreatic cancer cells orthotopically into the pancreas of age-matched male, athymic nu/nu mice and started treatment 2 weeks after tumor cell inoculation. JNKi (1 mg/kg) was administered orally five times a week, TRAIL (1 mg/kg) intraperitoneally twice a week, and gemcitabine (80 mg/kg) twice a week (to permit comparison of JNKi and TRAIL treatments to standard therapy). After 4 weeks of treatment, we found that the weights of L3.6pl tumors in mice treated with the combination of JNKi and TRAIL (JNKi/TRAIL) were significantly lower than those in mice treated with vehicle or TRAIL alone (FIG. 6B). MiaPaCa2 tumors showed a less prominent reaction to JNKi/TRAIL treatment in terms of tumor count (Table 1) and tumor weight (FIG. 6C). However, in mice inoculated with MiaPaCa2 cells, the total number of metastases, a hallmark of CSCs, was significantly reduced in JNKi/TRAIL-treated mice compared to control mice as well. (Table 1).

TABLE 1

Metastatic Burden of MiaPaCa2-inoculated Mice

| MiaPaCa2 | #tumors at 6 wks | % tumor presence at 6 wks | Liver mets | Spleen mets | Peritoneal mets | Kidney mets |
|---|---|---|---|---|---|---|
| control | 10/10 | 100 | 1 | 5 | 3 | 1 |
| JNKi | 4/4 | 100 | 1 | 1 | 0 | 0 |
| TRAIL | 10/10 | 100 | 2 | 0 | 1 | 0 |
| J/T | 9/10 | 90 | 0 | 5 | 0 | 0 |
| GEM | 5/5 | 100 | 1 | 3 | 1 | 0 |

Figure 6E:
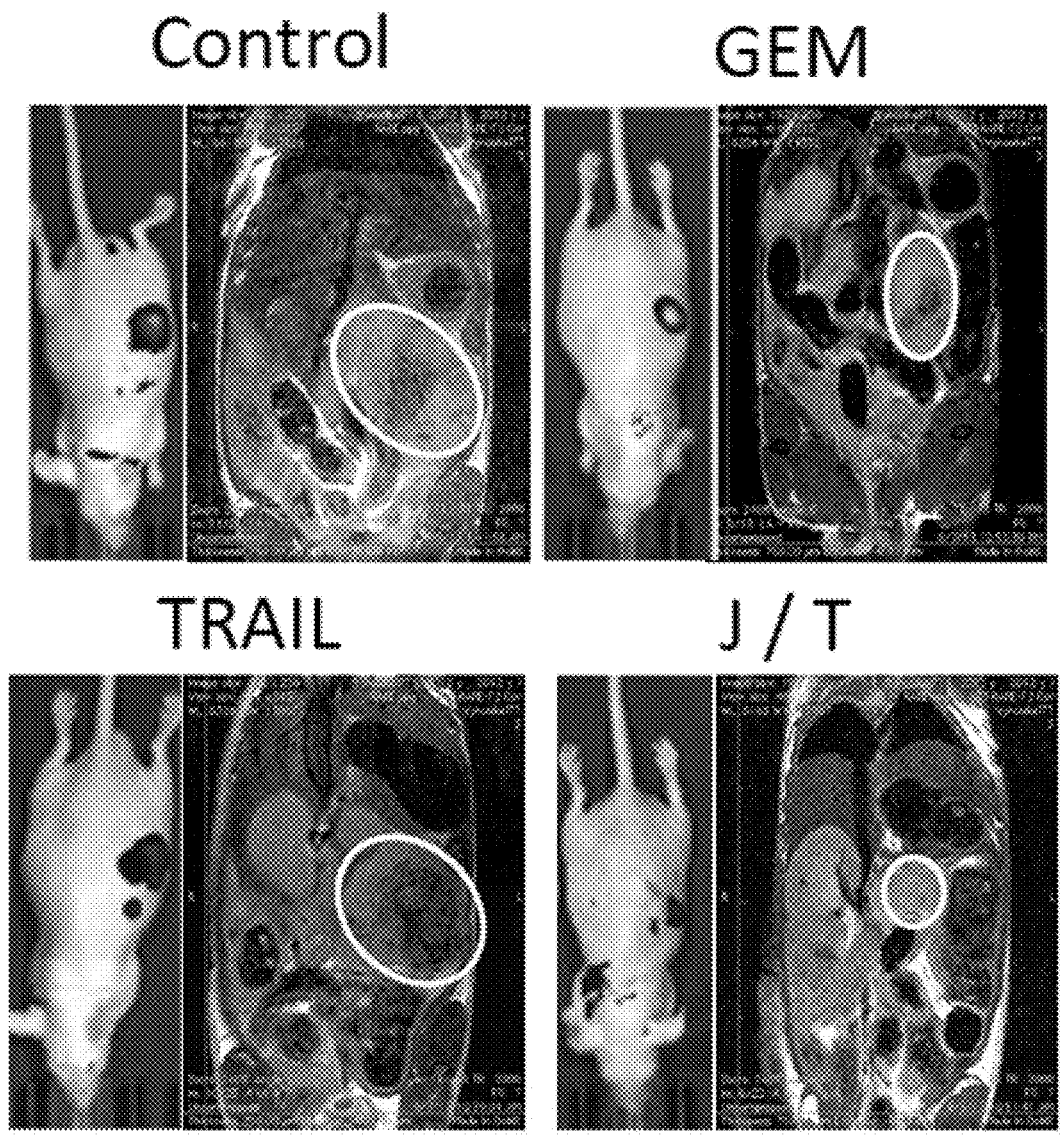
Figure 6F:
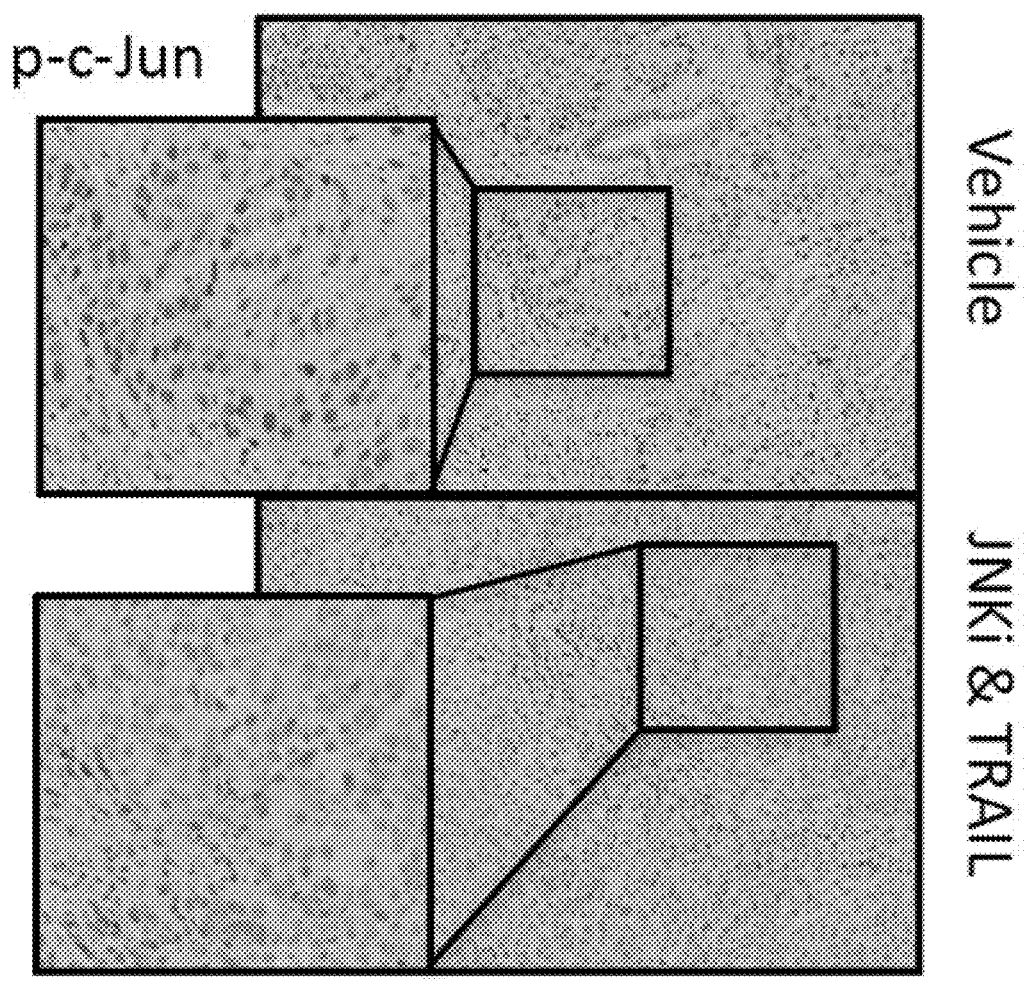
Figure 7:
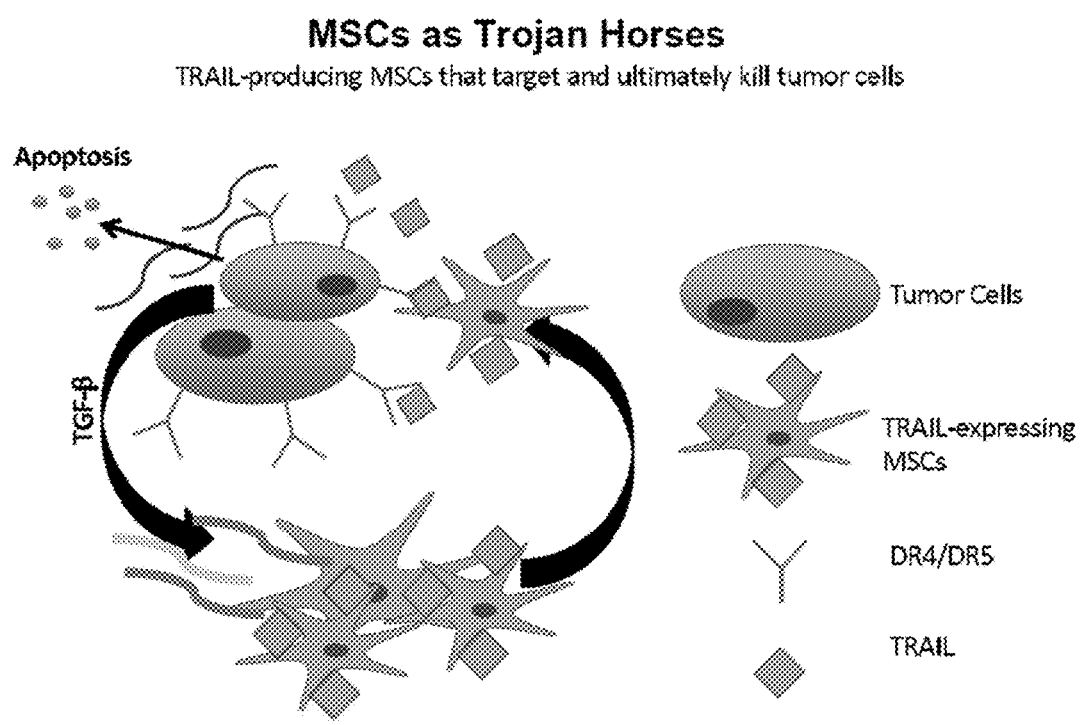
FIG. 7 represents a cartoon of the pathway of TRAIL induced apoptosis when delivered by genetically engineered MSC.

To further investigate these findings, we treated firmly established tumors. Panc1 cells were orthotopically injected into age-matched male, athymic nu/nu mice, tumor growth was confirmed by magnetic resonance imaging (MRI) and IVIS (FIG. 6E, right panels), and treatment was started after 28 days. We found markedly decreased tumor weights in mice treated with JNKi/TRAIL compared to mice treated with TRAIL alone or given vehicle control (FIG. 6D). As we observed in vitro, we found that p-c-Jun expression was profoundly reduced in sections of tumors treated with JNKi/TRAIL compared to vehicle control (FIG. 6F). In fact, established tumors seemed to respond early to treatment with JNKi/TRAIL as determined by in vitro imaging system and MRI (FIG. 6E).

Together, these findings convincingly demonstrate that low-dose JNKi/TRAIL treatment significantly reduces tumor growth both in TRAIL-sensitive tumors and even reduce tumor size and incidence of metastasis in TRAIL-resistant tumors to a greater extent.

Example 2: Materials and Methods

Jun N-terminal kinase inhibitor II SP600125 (JNKi) was obtained from Calbiochem, recombinant human TRAIL (rhTRAIL) from R&D Systems, and Gemcitabine from Elly Lilly. Products were reconstituted as recommended by the manufacturer. The following antibodies were used: phospho-c-Jun (Cell Signaling Technologies), CD133-APC (Miltenyi Biotech), and SSEA1-FITC (Santa Cruz Biotechnology, Inc.).

Cell Isolation and Culture:

Panc1 (obtained from American Type Culture Collection), MiaPaCa2, L3.6pl, Patx1, and HS766T pancreatic cancer cells (kind gifts of Dr. Kenji Yokoi) were maintained in minimum essential medium (MEM; Corning Incorporated) supplemented with 10% fetal bovine serum (FBS; Atlanta Biologicals), 1% penicillin-streptomycin, L-glutamine, MEM nonessential amino acids (all from Corning), and MEM vitamin solution (Gibco) at 37° C. in 5% $CO_2$. Medium was changed every 3 days, and cells were passaged before reaching 80% confluence. For experiments under hypoxic conditions, cells were cultured in the humidified modular hypoxia chamber (Billups-Rothenberg), which contained a 95% $N_2$ and 5% $CO_2$ mixture.

Sphere Culture and Sphere Forming Assay:

Sphere-forming medium consisted of MEMα supplemented with L-glutamine, putrescine, insulin (all from Sigma-Aldrich), epithelial growth factor (20 ng/mL), basic fibroblast growth factor (10 ng/mL), and B-27 supplement (Gibco). For first generation, attached cells were trypsinized, washed twice with PBS, and seeded in sphere-forming medium as single cell suspensions with clonal density (5,000-10,000 cells/mL) on ultra-low-attachment plates (Corning). After 7 to 10 days, spheres were harvested by gravitation in a tube, trypsinized, washed twice with PBS, and reseeded as described above for the next higher generation. To quantify sphere-forming ability, cells were prepared as described in the preceding paragraph and seeded in 96-well ultra-low-attachment plates at 500 to 1000 cells per well. Medium was supplemented with 1% methylcellulose to prevent cell-cell attachments. Medium was added or renewed every 3 days, and spheres were quantified at day 10 to 12.

Isolation of Human Adipose-Tissue-Derived Stem Cells:

Human subcutaneous adipose tissue was obtained from patients undergoing elective lipoaspiration with informed consent (The University of Texas MD Anderson Cancer Center Institutional Review Board registrations IRB00001035, IRB00003657, IRB00004920, and IRB00006075). Adipose tissue was washed thoroughly, minced, and incubated with Ringers lactate containing a combination of collagenase I and II and a neutral protease (MATRASE™ Reagent, InGeneron Inc. Houston Tex.) in a Tissue Processing Unit (TRANSPOSE® System, InGeneron Inc. Houston Tex.) for 30 minutes at 40° C. Subsequently, the cell suspension was filtered through a 100-μm filter, washed twice, and then centrifuged at 600 rpm for 5 minutes. The adipose stromal vascular fraction was resuspended in αMEM with 20% FBS, L-glutamine, and penicillin-streptomycin-amphotericin B (Sigma-Aldrich) at 37° C. in 5% $CO_2$. Red blood cells in the supernatant and nonadherent cells were removed after 48 hours. For all experiments shown, human subcutaneous adipose tissue-derived cells were used prior to passage 6.

Mtt Assay:

Cells were seeded in a 96-well plate at a density of 4000 to 5000 cells per well (70%-80% confluence) in triplicate. Non-adherent cells were washed with PBS, and different substrate dilutions were added. After 24 hours, 3-(4,5-dimethylthiazol-2-yl)-2,5-diphenyltetrazolium bromide (MTT) assay (Roche, Mannheim, Germany) was performed according to the manufacturer's instructions. Results were measured at 570 nm and background at 650 nm on a microplate reader (Molecular Devices).

Proliferation Assay:

For measurement of cell proliferation, cells were seeded into 24-well plates. After 24 hours, cells were washed with PBS, and medium with different dilutions of JNKi was added. Viable cells were then counted daily with a standard trypan blue stain protocol.

Invasion Assay:

Pancreatic cancer cells were pretreated in six wells for 24 hours with JNKi or control medium. Viable cells were then transferred to 24-well matrigel-coated invasion chambers with 8-mm pore size (BD Biosciences) in MEM with 1% FBS in the upper chamber and 500 µL of medium with 10% FBS in the lower chamber as a chemoattractant. After 24 hours, medium was removed, inserts were washed with PBS, and noninvaded cells were carefully removed. Cells on the bottom of the insert were fixed with ice-cold MeOH for 10 minutes, stained with crystal violet, and counted by light microscopy.

Colony-Forming Assay:

Cells were pretreated with JNKi as described in the preceding section. Five hundred viable cells were seeded in triplicate into a six-well plate with 3 mL of medium and incubated without change of medium. After 10 days, colonies were washed, fixed, and stained with crystal violet. Colonies were counted in four different view fields.

Two-Dimensional Wound Healing Scratch Assay:

Ninety-percent-confluent pancreatic cancer cell layers were scratched with the tip of a 10-µL pipette, washed with PBS, and further cultured with and without JNKi. Gap distances were measured by light microscopy at 0 hours, 16 hours, and 32 hours. Migration movement was measured in nine different fields. For immunofluorescent staining, the scratch assay was performed on a glass cover slide, and cells were then fixed, permeabilized with 80% EtOH, and stained with p-c-Jun primary antibody (Cell Signaling), Alexa-594-conjugated anti-rabbit secondary antibody, and DAPI for counterstaining of nuclei.

Acridine Orange/Ethidium Bromide Staining:

According to a protocol adapted from Todaro et al. (supra), attached cells or spheres were washed with PBS, stained with acridine orange/ethidium bromide, and visualized immediately with fluorescent microscopy.

Flowcytometric Evaluation of Apoptosis:

For the distinction of early and late apoptotic or necrotic events after treatment as described in the text, flowcytometry with the FITC Annexin V Apoptosis Detection Kit II (BD Pharmingen™) was carried out. Briefly, after treatment, cells were trypsinized, stained for 15 min at RT (25° C.) in the dark and analyzed within 1 hr according to the manufacturer's instructions.

Quantitative Reverse Transcription-PCR:

For total RNA extraction, cells were homogenized with TRIzol (Invitrogen). Phase separation was performed by the addition of chloroform and subsequent centrifugation steps. Aqueous phase of samples was collected, and RNA was precipitated by isopropyl alcohol. After washing, RNA was redissolved in DEPC-treated water, and RNA quality and quantity were measured with a Nanodrop ND-1000 Spectrophotometer (Thermo Scientific). For cDNA synthesis, the iScript Reverse Transcription Supermix (Bio-Rad) was used according to the manufacturer's protocol, and the reaction mix was incubated in a thermal cycler (Bio-Rad MyIQ Single-Color RT-PCR Detection System iCycler) with the following protocol: priming (5 minutes at 25° C.), reverse transcription (30 minutes at 42° C.), and reverse transcription inactivation (5 minutes at 85° C.). qRT-PCR was performed using iQ SYBR Green Supermix (Bio-Rad) according to the following protocol: initial denaturation and enzyme activation (1 cycle at 95° C. for 3 minutes), denaturing (40 cycles at 95° C. for 15 seconds) with annealing and extension (40 cycles at 55° C. for 30 seconds), and melting curve (1 cycle at 55° C.-95° C. in 5-° C. increments for 30 seconds). The Ct (cycle threshold) value was measured in absolute quantification (of cycles of amplification) and compared to β-actin, which served as a housekeeping gene.

PathScan p-SAPK/JNK Sandwich ELISA:

Protein lysates were obtained from adherent cells or spheres after 1-hour of incubation with JNKi and/or TRAIL. Protein quantification was performed, and PathScan Sandwich ELISA Antibody Pair (Cell Signaling Technologies) was performed according to the manufacturer's instructions.

Human CXCL8/IL-8 Immunoassay:

Cell culture supernatant was obtained after 24-hour treatments in triplicate. A human CXCL8/IL-8 Quantikine ELISA kit (R&D Systems) was used to measure human IL-8 according to the manufacturer's protocol. An IL-8 standard curve was performed to determine concentrations (in pg of cytokine per µL).

Differentiation Assay:

Adipose tissue-derived stem cells were seeded in the following concentrations: adipogenic differentiation, $1 \times 10^4$ cells/cm$^2$; chondrogenic differentiation, $1.6 \times 107$ cells/cm2; and osteogenic differentiation, $5 \times 10^3$ cells/cm$^2$. After a 2-hour incubation with 20% FBS-containing medium, cells were washed, and the respective differentiation media were added (Invitrogen StemPro differentiation kits). Differentiation media were changed twice a week. After 14 to 21 days, cells were fixed with 4% formaldehyde for 30 minutes and stained with Oil Red O for lipid vesicles (adipogenic differentiation), Alcian Blue for proteoglycans (chondrogenic differentiation), and Alizarin Red S for calcium deposits (osteogenic differentiation) as reported previously. Bai X, Alt E. "Myocardial regeneration potential of adipose tissue-derived stem cells" *Biochemical and Biophysical Research Communications*. 401 (2010) 321-6.

Animal Studies:

Age-matched male swiss nu/nu mice (6-8 weeks old) were injected orthotopically with pancreatic tumor cells. All procedures were performed in accordance with the guidelines of the Institutional Animal Care and Use Committee at The University of Texas MD Anderson Cancer Center (ACDF Protocol #12-12-12631). Animals were anesthetized with isoflurane anesthesia (1%-3% via inhalation), and an incision was made in the left abdominal flank. The spleen was located and extracted, and $1 \times 10^6$ pancreatic cells in 50 µL of PBS were injected into the underlying tail of the pancreas. The abdominal wall was closed with sterile absorbable sutures, and wound clips were applied to the skin. Animals were monitored daily and after two weeks of untreated tumor growth randomly assigned to different treatment groups: control (no treatment), JNKi (1 mg/kg) was administered by oral gavage five times per week; gemcitabine (80 mg/kg) or TRAIL (1 mg/kg) was injected intraperitoneally with a 27-G needle two times per week or JNKi and TRAIL together at the dosages indicated above. Weight, tumor growth, and health status were clinically followed for 4 weeks. At day 42, animals were euthanized, and blood and tissues were collected for postmortem analysis.

Statistical Analyses:

Results are expressed as the mean±standard of the mean. All statistical comparisons were made with a standard t-test or t-test with Welch's correction (where indicated), using biostatistics software from GraphPad Prism. For all comparisons, $p<0.05$ was considered statistically significant.

While this invention has been described with reference to illustrative embodiments, this description is not intended to be construed in a limiting sense. Various modifications and combinations of illustrative embodiments, as well as other embodiments of the invention, will be apparent to persons skilled in the art upon reference to the description. It is therefore intended that the appended claims encompass such modifications and enhancements.

We claim:

1. A method of treating pancreatic cancer in a patient comprising administration of a low-dose of a c-Jun N-terminal kinase (JNK) inhibitor of 1 mg/kg or less in combination with a low-dose of a TNF-related apoptosis-inducing ligand ("TRAIL") of 1 mg/kg or less.

2. The method of claim 1 wherein the low-dose of the JNK inhibitor and the low-dose of TRAIL are doses that do not significantly impact a rate of growth of the cancer if administered individually.

3. The method of claim 1, further comprising administering an antagonist to IL-8.

4. The method of claim 3, wherein the antagonist to IL-8 is a monoclonal antibody to IL-8.

5. The method of claim 3, wherein the antagonist to IL-8 is a monoclonal antibody to CXCR1.

6. The method of claim 1, where in the JNK inhibitor is administered orally and the TRAIL is administered by intraperitoneal injection.

7. A method of selectively inhibiting viability of a pancreatic cancer stem cell population in a cancer patient comprising administration of a low-dose of a c-Jun N-terminal kinase (JNK) inhibitor of 1 mg/kg or less in combination with a low-dose of a TNF-related apoptosis-inducing ligand ("TRAIL") of 1 mg/kg or less.

8. A method of treating pancreatic cancer in a patient comprising systemic administration of a low-dose of a c-Jun N-terminal kinase (JNK) inhibitor of 1 mg/kg or less orally in combination with localized administration of a dose of 1 mg/kg or less of a TNF-related apoptosis-inducing ligand ("TRAIL") in an organ or region of the patient where a tumor is present.

9. The method of claim 8, wherein the localized administration of TRAIL is obtained by introducing a recombinant TRAIL into a vessel or duct in direct fluid communication with the organ or region of the patient where the tumor is present.

* * * * *